US009258988B2

(12) United States Patent
Willenberg et al.

(10) Patent No.: US 9,258,988 B2
(45) Date of Patent: Feb. 16, 2016

(54) METHODS AND DEVICES FOR SUSTAINED RELEASE OF SUBSTANCES

(71) Applicants: UNIVERSITY OF FLORIDA RESEARCH FOUNDATION, INC., Gainesville, FL (US); George Georgiades, Lady Lake, FL (US)

(72) Inventors: Bradley J. Willenberg, Gainesville, FL (US); Philip G. Koehler, Gainesville, FL (US); Christopher D. Batich, Gainesville, FL (US); George Georgiades, Lady Lake, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 0 days.

(21) Appl. No.: 14/332,747

(22) Filed: Jul. 16, 2014

(65) Prior Publication Data

US 2015/0020439 A1    Jan. 22, 2015

Related U.S. Application Data

(60) Provisional application No. 61/846,848, filed on Jul. 16, 2013.

(51) Int. Cl.
*A01M 1/20* (2006.01)
*A01M 29/12* (2011.01)

(52) U.S. Cl.
CPC ........... *A01M 1/2055* (2013.01); *A01M 1/2027* (2013.01); *A01M 1/2044* (2013.01); *A01M 29/12* (2013.01)

(58) Field of Classification Search
CPC ............ A01M 1/2022; A01M 1/2027; A01M 1/2044; A01M 1/2055; A01M 29/12

USPC .......................................... 43/124, 131, 132.1
See application file for complete search history.

(56) References Cited

U.S. PATENT DOCUMENTS 3,169,705 A * 2/1965 Geiger .......................... 239/43
3,826,036 A * 7/1974 Neugebauer ................... 43/131

(Continued)

FOREIGN PATENT DOCUMENTS

CN      202890168 U   4/2013
EP      0669137 A1    8/1995

(Continued)

OTHER PUBLICATIONS

Müller, G.C. et al., "Efficacy of the botanical repellents geraniol, linalool, and citronella against mosquitoes," *Journal of Vector Ecology*, Jun. 2009, pp. 2-8, vol. 34, No. 1.

(Continued)

*Primary Examiner* — David Parsley
(74) *Attorney, Agent, or Firm* — Saliwanchik, Lloyd & Eisenschenk

(57) ABSTRACT

Devices that provide timed-release of target compounds absorbed by, or otherwise integrated into, an external housing. The external housing absorbs and facilitates volatilization of the released compound. A permeable cover can be employed as a regulating mechanism to control the rate volatilization from the external housing. One or more reservoirs containing target compound can be contained within one or more internal chambers of the external housing. The one or more reservoirs can release the target compound for absorption by the external housing and/or to make contact with one or more other reservoirs so as to compromise the other reservoirs and release target compound within. A wick can be employed in certain embodiments to transfer target compound from the internal chamber to the external housing to be volatilized. Continued or sequential release of target compound to recharged the external housing achieves a zero order release rate from the external housing.

19 Claims, 15 Drawing Sheets

(56) References Cited

U.S. PATENT DOCUMENTS

| | | | |
|---|---|---|---|
| 4,037,353 A * | 7/1977 | Hennart et al. | 43/129 |
| 4,158,440 A * | 6/1979 | Sullivan et al. | 239/6 |
| 4,562,794 A | 1/1986 | Speckman | |
| 4,690,825 A | 9/1987 | Won | |
| 4,930,451 A * | 6/1990 | Miller et al. | 119/654 |
| 5,688,509 A | 11/1997 | Radwan et al. | |
| 5,858,385 A | 1/1999 | Sirkar et al. | |
| 5,975,427 A * | 11/1999 | Harries | 239/34 |
| 6,109,539 A | 8/2000 | Joshi et al. | |
| 6,296,866 B2 * | 10/2001 | Karg | 424/409 |
| 6,513,726 B1 | 2/2003 | Esteban Duran | |
| 6,936,269 B2 | 8/2005 | Robinson | |
| 7,544,332 B2 | 6/2009 | De Silva et al. | |
| 7,622,134 B2 * | 11/2009 | Davis et al. | 424/421 |
| 7,988,984 B2 | 8/2011 | Hockaday | |
| 2006/0270737 A1 | 11/2006 | Matias | |
| 2008/0311008 A1 | 12/2008 | Tranzeat | |
| 2010/0108778 A1 | 5/2010 | Greenland | |
| 2010/0314461 A1 | 12/2010 | Gruenbacher et al. | |
| 2011/0159064 A1 | 6/2011 | Kawaguchi et al. | |
| 2011/0259064 A1 | 10/2011 | David et al. | |
| 2011/0303757 A1 | 12/2011 | Blondeau et al. | |
| 2012/0270944 A1 | 10/2012 | Zhang et al. | |
| 2013/0095162 A1 | 4/2013 | Quinn | |

FOREIGN PATENT DOCUMENTS

| | | |
|---|---|---|
| EP | 2529628 A1 | 12/2012 |
| WO | WO 00/74490 | 12/2000 |
| WO | WO 2006/061803 | 6/2006 |

OTHER PUBLICATIONS

Off! Clip-On Starter Kit product information, [online, webpage, retrieved Jan. 30, 2015] from: http://www.amazon.com/OFF-70318-Off-Clip-On-Starter/dp/B001H1JJHG, p. 1.

Fly Leg Bands for Horses product information, [online, webpage, retrieved Jan. 30, 2015] from: http://www.jefferspet.com/products/fly-leg-band-1-sz-fits-all-set, p. 1.

Dairy Aerosols & Fly Sprays product information, [online, webpage, retrieved Jan. 30, 2015] from: http://www.country-vet.com/applications.aspx, pp. 1-2.

Equine Products product information, [online, webpage, retrieved Jan. 30, 2015] from: http://www.country-vet.com/products.aspx?cat_id=3, pp. 1-2.

ThermaScent™ Scent Dispenser—Starter Kit product information, [online, webpage, retrieved Feb. 2, 2015] from: http://www.thermacell.com/mosquito-repellent/accessories/thermascent-scent-dispenser-starter-kit, p. 1.

* cited by examiner

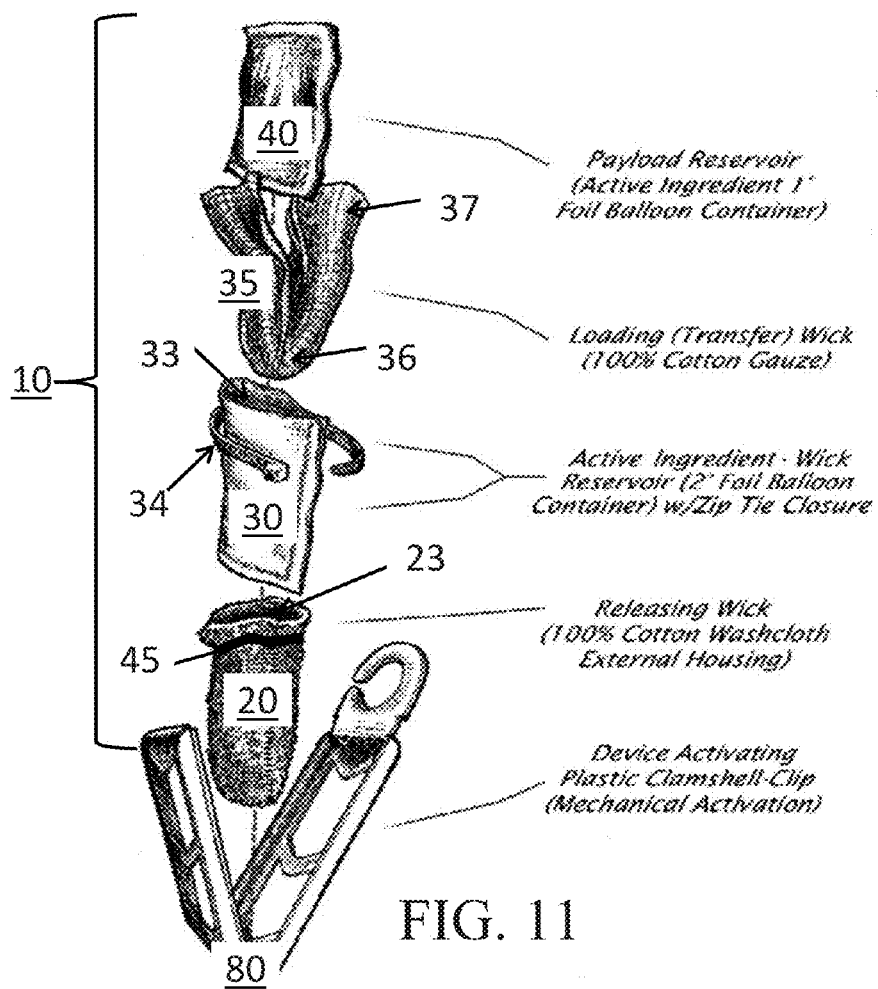
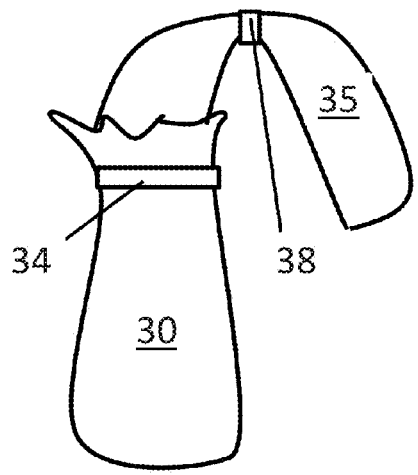
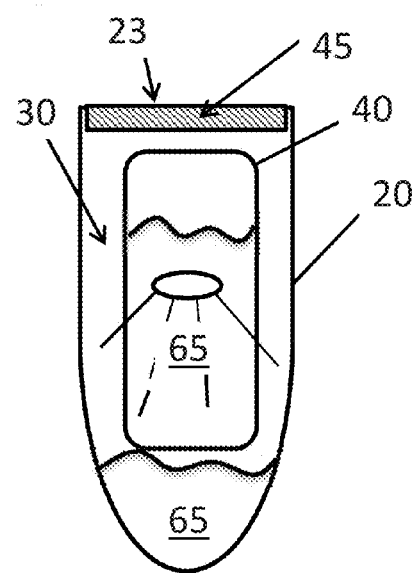
FIG. 11
FIG. 15
FIG. 14

METHODS AND DEVICES FOR SUSTAINED RELEASE OF SUBSTANCES

CROSS-REFERENCE TO RELATED APPLICATION

The present application claims the benefit of U.S. Provisional Application Ser. No. 61/846,848, filed Jul. 16, 2013, which is hereby incorporated by reference herein in its entirety, including any figures, tables, or drawings.

BACKGROUND OF INVENTION

There are numerous substances for which sustained, airborne release of controlled concentration is desirable. Of particular interest worldwide are methods and devices capable of releasing substances that repel insects, particularly biting or disease vectoring species. Some of the most effective substances for repelling insects tend to have a high volatility, which allows them to spread more easily throughout an area making them effective spatial repellents. An unfortunate consequence of this high volatility is that they are short-lived and susceptible to environmental factors such as wind, humidity, and temperature.

There is also some evidence that long-range dispersal caused by saturation of a given area can send confusing signals that indicate the presence of a host and actually attract, rather than repel, insects to the area. (M. Debboun, S. P. Frances, and D. Strickman. 2007. Insect Repellents: Principles, Methods, and Uses. pgs. 13-14, CRC Press, Boca Raton, Fla.). However, some substances are specifically utilized because they have the ability to attract insects. Often, eradication of an insect necessitates that it be attracted to the control or eradication means, whether it be chemical, biological, or mechanical. Some biocontrol substances require contact with, or even ingestion by, an insect. Thus, dispersal mechanisms of a substance that will attract an insect to a specific area are often utilized.

A variety of release mechanisms, including various apparatuses, materials, formulations, and techniques, have been developed to try to provide a sustained, controlled release of volatile substances. Typically, these devices release an initial high concentration, which then tapers off, releasing less of the substance over time. As the amount of substance being released lessens, it can eventually become ineffective, often before the repellent is exhausted. Various binding agents or additives can be added to the repellent to try to slow and control the release and provide longer protection. But these agents and additives dilute the repellent and usually reduce their effectiveness more quickly. Depending upon the release apparatus, the type of substance, repellent or attractant, and environmental factors, an effective amount of the substance can be provided for a few hours and maybe up to a few days before the release mechanism has to be replaced or recharged.

In some situations, it is not possible or feasible to replace or recharge a substance release mechanism regularly or within a short period of time. One example is the use of repellents with livestock. It is well-known that livestock can benefit significantly by reduction of insect annoyance. For livestock farmers and animal breeders, particularly horse and cattle breeders, fighting pests is one of the most expensive and time-consuming issues that they deal with daily. The use of spatial repellents is usually not feasible with roaming livestock. Thus, more common techniques for controlling livestock pests include release mechanisms such as dust bags, impregnated ear tags, repellent misters, or other direct external repellent application to the animal. Pests in animal housing, i.e., barns, stalls, pens, etc., are often controlled with spatial release mechanisms that provide protection within a given area. However, all of these mechanisms exhibit the same disadvantages discussed above, an initial, usually short-term, effectiveness tapering off to an ineffective concentration within a relatively short time period. Needless to say, for a large animal herd, or animals scattered over a large area, repeated applications or recharging of repellent release mechanisms can be tedious and time-consuming.

There is an ongoing need for a release mechanism that can operate with short-lived, volatile insect repellents, attractants, biopesticides, pesticides, or other active ingredients to increase their efficacy and effectiveness over a longer period of time. A release mechanism that can provide an efficient spatial dispersal system with sustained release at optimal levels would be advantageous. Such a release mechanism, could achieve effective levels of protection with less toxic or harsh active ingredients, if such ingredients could be sustained at effective levels. Ideally, such a device would be amenable for use in stationary or mobilized applications, such as, for example, on or around roaming livestock or within their living areas.

BRIEF SUMMARY

Some of the most effective insect repellents or attractants are often characterized as, or utilized with, high volatility compounds. The effectiveness of such substances is directly related to the release mechanisms utilized and the ability of those mechanisms to maintain sufficient, affective concentration levels in and around an area. Most release mechanisms provide an initial high concentration level that tapers off, for a period of time, maintaining a level of effective concentration before eventually releasing ineffective concentration levels. Often the ineffective concentration levels are reached before the repellent is fully exhausted from the device, which can result in wasted material. Various methods are used to increase effectiveness of repellents over a longer period of time. Most of these methods require dilution of the effective ingredient, necessitating the use of greater amounts, or harsher substances, to achieve effective repellency.

In accordance with embodiments of the subject invention, the problems associated with release mechanisms used with volatile insect repellents are solved with devices that "containerize" repellents, attractants, pesticides, biopesticides, and other target compounds, a.k.a., active ingredients, within reservoirs of inert, non-permeable materials. The embodiments of the subject invention further provide an efficient dispersal system and optimal sustained release devices. Such devices can, in certain embodiments, permit use of less toxic ingredients to achieve the required efficacy.

Embodiments of the subject invention accomplish the objective of sustained, effective release of a target compound with devices comprising 1) one or more of a unique method of activation, 2) replenishment with the use of reservoirs, which contain one or more active target compounds, and 3) a dispersal mechanism that can be utilized with and replenished repeatedly with target compounds released from one or multiple reservoirs. Further embodiments employ one or more compounds or substances that can permeate the reservoirs to release the target compounds therein. Embodiments of the subject invention can be used advantageously as individualized insect repellent systems, such that they are useful for human or animal use, for example, on or around livestock or other animals or attached to clothing or personal equipment. Specific embodiments are amenable to actual attachment to an individual, human or animal, so as to provide an effective level of insect repellent in a spatial area around the animal for a longer period of time. Other embodiments can be employed in areas away from human or animal habitation and attract insects for eradication. Alternative embodiments of the subject invention can be utilized to control insects within a spatial area by attachment to a structure or object.

Certain embodiments of the device can be activated by a container, such as after removal from a container and in certain other embodiments the container itself can assist in triggering the device. Reservoirs can be used to isolate one or more compounds inside a housing apparatus. The housing apparatus can be stored within the container and can, in certain embodiments, aid in keeping the device and/or target compound separated and/or inactive and provide significant shelf-life for the product. The housing, or components thereof, can aid in the dispersal of the target compound after being released inside the housing or an internal chamber within the housing. In one embodiment, a target compound directly contacts the housing and permeates through the one or more materials of the housing to be dispersed from the surface of the housing. In another embodiment, a wick-like mechanism is in contact with a target compound within the housing and transfers the target compound to the housing for dispersal from the surface of the housing.

Specific embodiments of the device utilize one or more materials to form a housing having one or more internal cavities, in which are disposed at least one reservoir having walls or membranes. The walls or membranes that form the reservoir can be one or more materials that are, ideally, impermeable to the target compound(s) stored within the reservoir or are at least substantially impermeable to the target compound(s), such that long-term storage is possible without appreciable loss in volume of the target compound (s) through the walls or membranes of the reservoir.

This advantageous feature of certain embodiments disclosed herein allows the devices to be stored with target compounds therein until such time as they are required to be deployed. FIG. 12B illustrates one non-limiting example where multiple tests were conducted with an embodiment of the device utilizing citronella oil, thyme oil, and a citronella oil and geraniol oil (50:50) composition. Each testing device was stored with their respective target compounds in an impermeable, unruptured reservoir, according to the subject invention, for approximately 125 hours. The graph in FIG. 12B illustrates that there was no appreciable release of target compound during the 125 hour period. However, when the reservoirs were ruptured after 125 hours, the graph shows that each device exhibited a significant increase in release rate of their respective target compounds.

In one embodiment, at least one of the reservoirs can be disrupted mechanically, chemically, by environmental factors, or some combination thereof. The reservoir can also be disrupted by interaction with or by action of the container in which it is stored, for example, when the device and/or reservoirs are removed from, placed into, or otherwise interact with some part of the container, the container can release the target compound from the reservoir. In another embodiment, the reservoir walls or membranes comprise one or more material(s) that can be chemically degraded, fragmented, ruptured, solvated, or otherwise damaged or compromised to facilitate a sequential- or timed-release of volatile repellants, pesticides, or other target compounds. By way of one non-limiting example, reservoirs within the device can contain different substances that are timed to be released from the reservoirs at different intervals of the day to control insects with different active periods. For example, one compound can be released early in the day to control diurnal insects and another compound can be timed to release at sunset to control nocturnal insects. By way of another non-limited example, reservoirs within the device can contain substances for controlling a specific type of insect and are configured to release that substance when one or more certain environmental factors, e.g., rain or specific temperature(s) occur. When released, the compounds are absorbed by the outer material, from which the compound can then diffuse or volatilize throughout a spatial area.

In a particular embodiment, the target compound itself is also capable of compromising the integrity of one or more other reservoirs. With this embodiment, the target compound can be released from a reservoir to be absorbed by material of the housing, while at the same time working to disrupt one or more other reservoirs disposed within the internal cavity of the outer material. In a more specific embodiment, as the concentration of the target compound diminishes, such as by evaporation or volatilization, from the outer material, one or more of the other reservoirs within the internal cavity will be sufficiently compromised that it can rupture, releasing more target compound. This released target compound will be absorbed by and can recharge the material of the external housing, while at the same time beginning the process of compromising one or more other reservoirs. This cycle can be repeated until the final reservoir(s) has ruptured, so that, for a period of time, the outer material maintains a constant saturation level of target compound. As a result, the level of target ingredient within the spatial area can remain constant and at optimal or effective levels.

In another particular embodiment, a reservoir containing target compound is located within an impermeable internal chamber within the housing. The internal chamber can be impermeable to chemical, temperature, environmental, or other non-mechanical forms of degradation. Ideally, the internal chamber is also not readily susceptible to being mechanically compromised or opened. A wick can extend out from the impermeable internal chamber. The reservoir within the internal chamber can be mechanically compromised, releasing target compound into the impermeable, uncompromised internal chamber, which contains and isolates the target compound. The wick can be the mechanism that transmits the target compound from the internal chamber to the external housing, from which it can be dispersed.

Advantageously, the embodiments of the subject invention can be utilized with pure, undiluted target compounds. The embodiments can also be utilized with more than target compound simultaneously. The device allows for long-term storage with minimal or no loss of target compound and simple, effective devices and techniques for release of the target compound to activate the devices.

BRIEF DESCRIPTION OF DRAWINGS

In order that a more precise understanding of the above recited invention can be obtained, a more particular description of the invention briefly described above will be rendered by reference to specific embodiments thereof that are illustrated in the appended drawings. The drawings presented herein may not be drawn to scale and any reference to dimensions in the drawings or the following description is specific to the embodiments disclosed. Any variations of these dimensions that will allow the subject invention to function for its intended purpose are considered to be within the scope of the subject invention. Thus, understanding that these drawings depict only typical embodiments of the invention and are not therefore to be considered as limiting in scope, the invention will be described and explained with additional specificity and detail through the use of the accompanying drawings in which:

FIG. 11 is an illustration of the embodiment shown in FIG. 10 demonstrating how the different components are arranged in the device.

FIG. 14 is an illustration of one embodiment of a latex sleeve, according to the embodiments of the subject invention.

FIG. 15 is an illustration of an internal chamber with a wick extending therefrom showing where one or more constrictions in the wick can be formed in the wick.

DETAILED DISCLOSURE

Figure 1A:
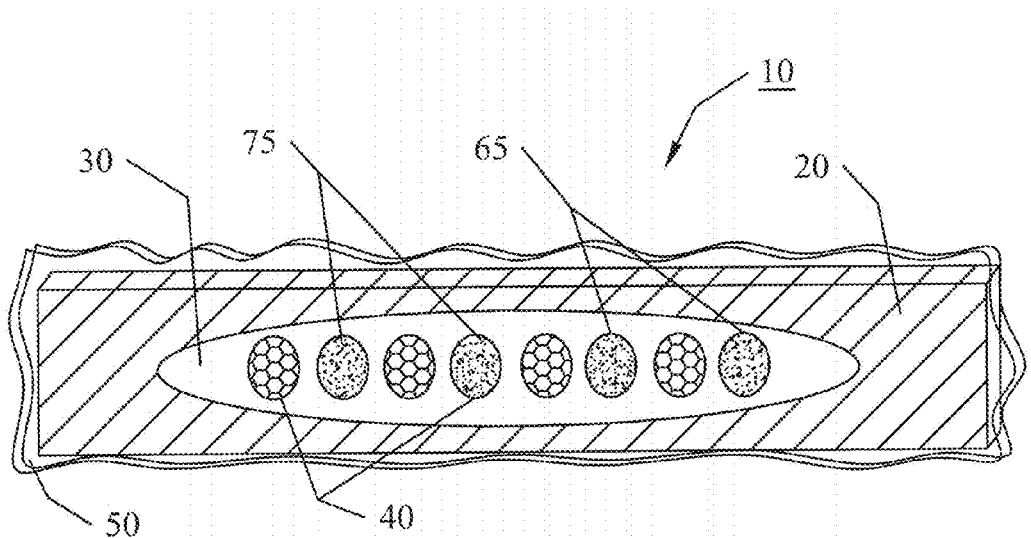
FIG. 1A illustrates an embodiment of the subject invention having an external housing with a single internal chamber with multiple reservoirs contained therein. The external housing is enveloped in a permeable cover.
Figure 1B:
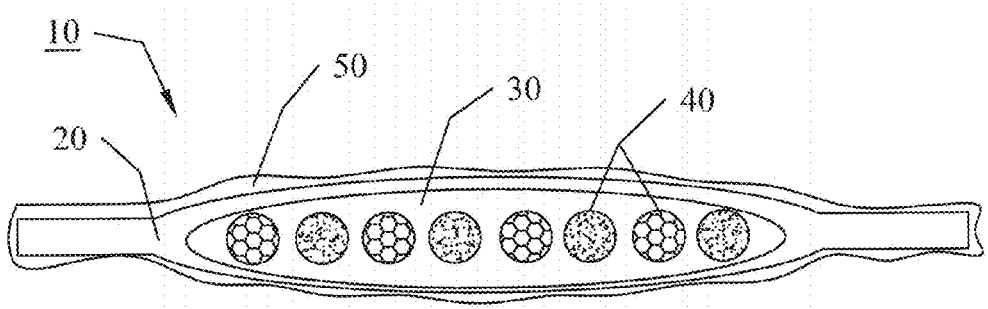
FIG. 1B is a side view of the embodiment shown in FIG. 1A.

The subject invention disclosure describes embodiments of devices for release and dispersal of target compounds, a.k.a., active ingredients. More specifically, the subject invention provides one or more embodiment(s) of devices capable of providing a constant or near constant concentration of a target compound, such that the devices are capable of providing a near zero order release and dispersal of a target compound within a spatial area.

The following description will disclose that the embodiments of the subject invention are particularly useful in the field of insect repellents, in particular, devices used for dispersing insect repellents throughout a 3-dimensional or spatial area. However, a person with skill in the art will be able to recognize numerous other uses that would be applicable to the devices and methods of the subject invention. While the subject application describes, and many of the terms herein relate to, a use for repelling insects, other modifications apparent to a person with skill in the art and having benefit of the subject disclosure are contemplated to be within the scope of the present invention.

In the description that follows, a number of terms are used. In order to provide a clear and consistent understanding of the specification and claims, including the scope to be given such terms, the following definitions are provided.

The term "insect" as used herein, describes any arthropod species desired to be controlled, in particular, species known for biting, stinging, or annoyance behaviors, as well as disease vectoring species. This can include, but is not limited to, mosquitoes, flies, ticks, lice, fleas, wasps, bees, cockroaches, ants, bedbugs, etc. However, the devices of the subject invention can also be utilized with other arthropod or even non-arthropod species. Thus, it should be understood that the term "insect" is used for literary convenience and is not meant to imply any limitation regarding the use of the embodiments of the subject invention.

The terms "repellent," "active ingredient," and "target compound" are used herein only for literary convenience to refer to any substance desired to be dispersed. The embodiments of the subject invention can be used with any suitable substance, which would include those that repel or attract an insect or that in some way cause an insect to make oriented or deliberate movements relative to the embodiments of the subject invention. The term can also include compounds known to actively control or eradicate insects, such as, for example, permethrin, deltamethrin, DEET, metafluthrin, and other chemicals and substances. Thus, these terms as used herein broadly encompass substances that repel or attract insects, but also include pesticides, including biopesticides, hormones, pheromones, combinations thereof, or any other substance that affects the behavior or biology of an insect. In addition, any of a variety of one or more perfumes, fragrance oils, deodorizers, disinfectants, or other substances desired to be dispersed or volatilized within or around an area are understood to be included under this term.

Also, as used herein, and unless otherwise specifically stated, the terms "operable communication," "operable connection," "operably connected," "cooperatively engaged" and grammatical variations thereof mean that the particular elements are connected in such a way that they cooperate to achieve their intended function or functions. The "connection" or "engagement" may be direct, or indirect, physical or remote In addition, references to "first", "second", and the like (e.g., first and second reservoir), as used herein, and unless otherwise specifically stated, are intended to identify a particular feature of which there can be at least two. Such reference to "first" does not imply that there must be two or more. However, these references are not intended to confer any order in time, structural orientation, or sidedness (e.g., left or right) with respect to a particular feature.

Finally, reference is made throughout the application to the "proximal side" and "distal side." For the sake of clarity, these terms are used herein simply to provide an understanding of the arrangement of certain components of the subject invention. Thus, the proximal side is referred to as that side that can be placed against a surface, such as, for example, against a wall, an individual, or against other components of the subject invention. Conversely, the distal side of the device is referred to as that side that would face away from a surface, or individual.

The present invention is more particularly described in the following embodiments and examples that are intended to be illustrative only since numerous modifications and variations therein will be apparent to those skilled in the art. As used in the specification and in the claims, the singular for "a," "an" and "the" include plural referents unless the context clearly dictates otherwise.

Reference will be made to the attached figures on which the same reference numerals are used throughout to indicate the same or similar components. With reference to the attached figures, which show certain embodiments of the subject invention, it can be seen that the subject invention comprises, generally, a release device 10 that comprises an external housing 20 having one or more internal chambers 30 into which are disposed one or more reservoirs 40 containing any one or more of a variety of triggering 65 and/or target compounds 75. In one embodiment, a permeable cover 50, having at least one and preferably a plurality of openings therethrough, surrounds at least a portion of the external housing. Most, or all, of the release device 10 can be disposed within a container 80. In particular embodiments, the container can be employed to activate or reactivate the release device. In certain other embodiments, the release device can comprise one or more materials that can be consumed by an insect.

Certain embodiments of the devices of the subject invention provide timed-release of one or more target compounds, which have been absorbed by or otherwise integrated into the external housing. Certain other embodiments provide for a controlled release of the target compound. With the embodiments of the subject invention, the external housing can act as a delivery vehicle for the target compound for diffusion into a surrounding spatial area.

Some other embodiments utilize a wick that replenishes the external housing at a sustained, controlled rate. With these embodiments, the wick can be in contact with the target compound, such that, by capillary action of the wick material, gravity, or other effect, the target compound is transferred to the external housing for dispersal.

Other embodiments can employ a permeable cover surrounding the external housing as a regulating mechanism to control the rate of diffusion of target compound from the external housing. The permeable cover can comprise a material or can have one or more openings that allow diffusion through the permeable cover of the target compound. In one embodiment, material of the permeable cover and/or the number and size of the openings formed within the permeable cover can be modified, depending upon a variety of factors that would be understood to those skilled in the art, so as to provide, as near as possible, a zero order release rate or diffusion rate of the target compound from the external housing. A zero order release rate can provide a constant or near constant concentration of a target compound within a given spatial area, depending upon prevailing environmental conditions. Certain embodiments of the subject invention can sustain a near zero order release rate that maintains a concentration in a spatial area that fluctuates by about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25%, and/or that fluctuates within a range between any two of the listed values.

Figure 2A:
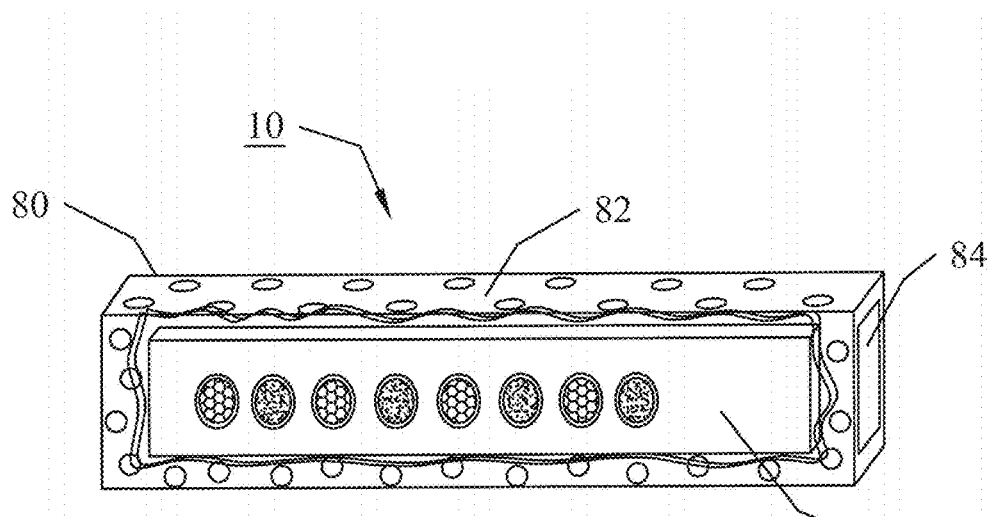
FIG. 2A is an alternative embodiment of the subject invention having an external housing with multiple internal chambers with a single reservoir in each. The external housing is shown enveloped in a permeable cover and the entire release device is secured within an embodiment of a container.
Figure 3A:
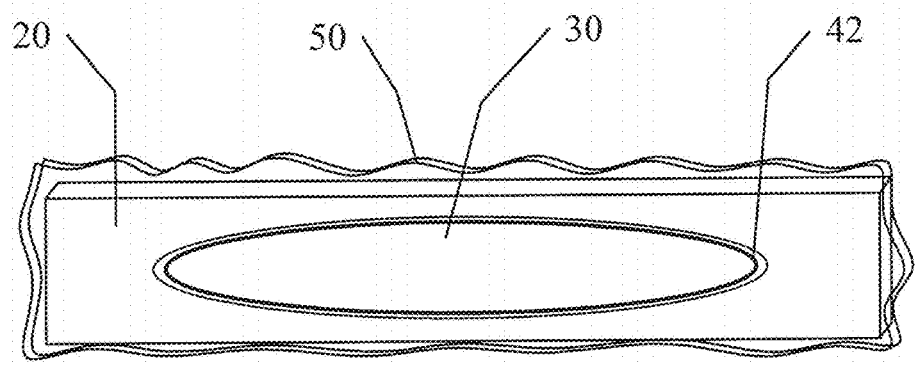
FIG. 3A is another alternative embodiment of the subject invention having an external housing with a single internal chamber lined with reservoir material. The external housing is enveloped in a permeable cover.
Figure 3B:
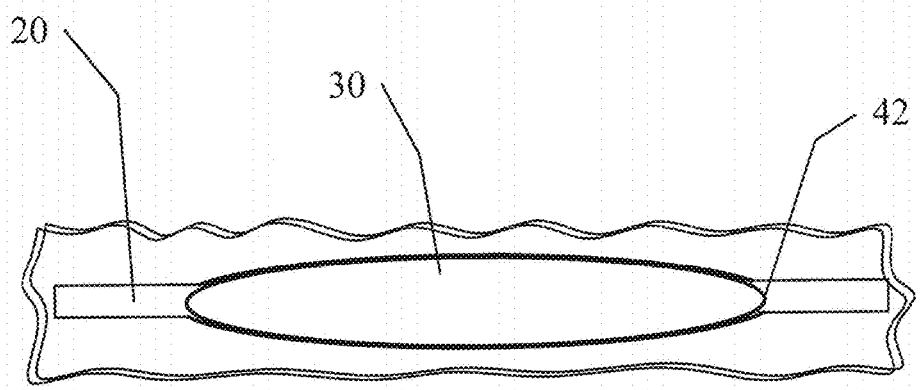
FIG. 3B is a side view of the embodiment in FIG. 3A showing an internal chamber lined with reservoir material.
Figure 5:
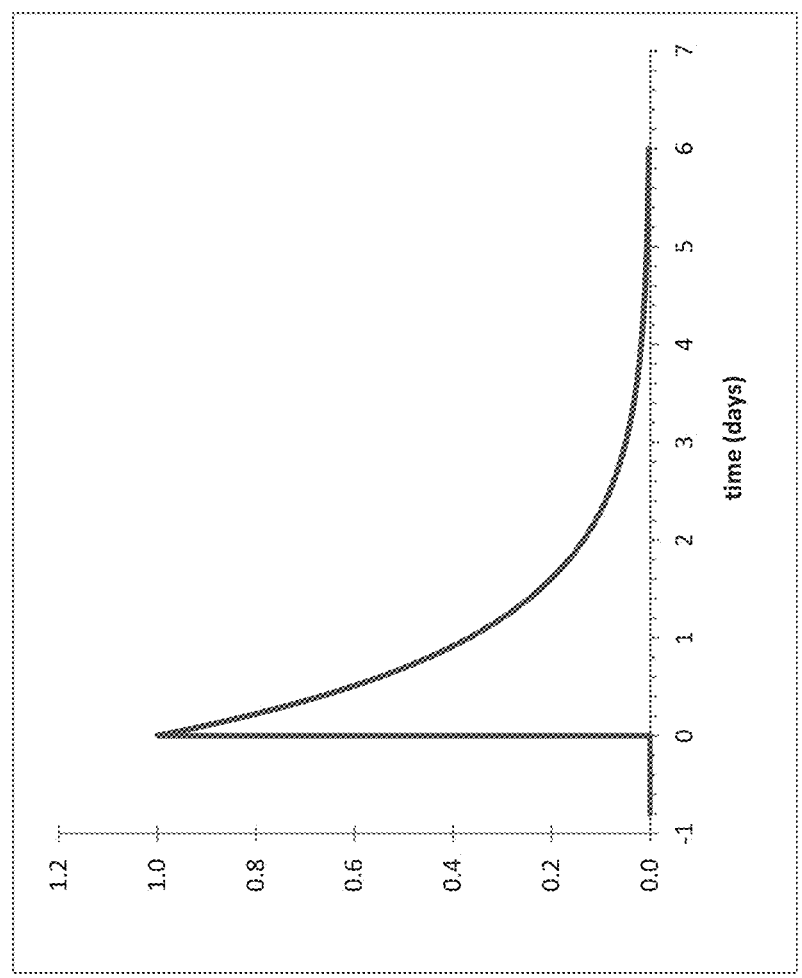
FIG. 5 illustrates an example of a first-order release rate observed with sustained delivery devices.

In specific embodiments, illustrated, by way of example, in FIGS. 1A, 2A, and 3A, one or more reservoirs 40 are contained within one or more chambers 30 of the external housing 20. The reservoirs can contain triggering compounds 65, as well as target compounds 75. In use, one or more of the triggering compound-containing reservoirs can be ruptured, broken, degraded, or otherwise mechanically or chemically compromised, so that the triggering compound is released, slowly or en masse, from the reservoir. In a particular embodiment, triggering compound is released first. Once released, the triggering compound can make contact with one or more other reservoirs containing a target compound. The released triggering compound then operates to degrade, dissolve, solvate, fragment, rupture, or otherwise compromise the target compound-containing reservoir. Once released, the target compound can be integrated, such as, for example, by absorption, into the external housing for diffusion through the permeable cover 50.

In certain embodiments, the triggering compound and target compound are different substances. These embodiments can require that the triggering compound be released first, so that it can act upon one or more target compound-containing reservoirs. In alternative embodiments, the triggering compound and target compound are the same or similar substance. With these embodiments, the initial target compound-containing reservoir is damaged or compromised, so that target compound can be released and integrated into the housing, while simultaneously operating to damage or compromise one or more other compound-containing reservoirs that are in the same or different chambers within the external housing.

In another embodiment, illustrated by way of example in FIGS. 10 and 11, at least one reservoir 40 is contained within one or more internal chambers 30 of the external housing 20. In a further embodiment, the internal chamber is made of a material that is impermeable to at least the target compound, and possibly other chemical, temperature, and environmental conditions. It can also be beneficial with this embodiment for the internal chamber to also be unaffected by mechanical forces that can be applied to the device, as discussed below.

The material of an internal chamber can be part of the external housing, wherein, for example, the material is fixedly attached or otherwise incorporated as part of the housing, such as in the form of a lining that forms a void within the housing. Alternatively, the internal chamber could be a separate component insertable into the internal housing, such as shown, for example, in FIGS. 11 and 12. One or more reservoirs therein can contain one or more target compounds 75. The one or more target compound-containing reservoirs can be ruptured, broken, degraded, or otherwise mechanically or, as in some embodiments, chemically compromised, so that the target compound is released en masse or incrementally from the one or more reservoirs and into the internal chamber. The internal chamber contains and isolates the target compound from contact with the external housing. However, once released, the target compound can make contact with one or more wicks 35 that extend from the internal chamber 30. In one embodiment, the wick moves the target compound from the internal chamber to the material of the external housing for dispersal. In a particular embodiment, a receiving end 36 of the wick is disposed within the internal chamber. In a more particular embodiment, the wick is disposed within the internal chamber sufficiently that all or most of the target compound can make contact with the wick 35. This can aid in all or most of the target compound being eventually moved to the external housing. FIGS. 10 and 11 illustrate non-limiting examples, where the receiving end 36 of the wick fills all or most of the internal chamber 30 and surrounds the reservoir 40. When the target compound is released from the reservoir, all or most of the target compound will be able to make contact with the receiving end of the wick for removal to the housing.

Ideally, a delivering end 37 of a wick can further make sufficient contact with the external housing so that the target compound from the receiving end 36 migrates, transfers, leaches, or is otherwise transferred from the internal chamber to the external housing. The target compound can also be dispersed from the wick. However, the advantage of transferring the target compound to an external housing is that the external housing can provide a greater surface area from which the target compound can be released. This can aid in ensuring that an adequate concentration of the target compound is maintained in a given spatial area to provide the desired effect on insects.

The wick can be made of one or more materials capable of moving the target compound by, for example, capillary action, through the wick. In one embodiment, the wick is made of a fibrous material. In another embodiment, the wick is a sponge or sponge-like material, such as, by way of non-limiting example, an open-cell foam material. In a more specific embodiment, the wick is made of a material that is at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 100% cotton and/or a material that includes an amount of cotton in a range between any two of the listed values. In a particular embodiment, the wick is a terry cloth material, such as the type usually used for bathing towels or washcloths. However, it is within the skill of a person skilled in the art to determine any of a variety of materials that could be utilized for a wick of the subject invention. Such variations, which provide the same function, in substantially the same way, with substantially the same result, are within the scope of this invention.

FIGS. 12C and 13 are graphs illustrating the different release rate results obtained from devices utilizing a wick in contact with an internal reservoir containing citronella oil, geraniol oil, thyme oil, metafluthrin, or combinations thereof, and an isopropanol control. It can be seen that embodiments utilizing a wick in contact with a dispersing external housing provide an increase in the amount of material released over time and then levels off to a relatively consistent release rate. The rapid increase can be due to the external housing becoming more saturated with the target compound, until it reaches a maximum saturation level and exhibits a steady, controlled dispersal of the target material from the surface of the external housing.

It can be preferable for the release device 10 to be as functional as possible upon immediate deployment. Furthermore, depending upon the materials utilized for the external housing 20, and wick 35, the target substance, expected areas of use, and other factors that would be understood by a person skilled in the art, it may not be possible or preferable for reservoirs to contain sufficient material to adequately saturate and/or activate the external housing and/or one or more wicks, such that sufficient material can be immediately diffused or volatilized to effect repellency. Therefore, in particular embodiments of the subject invention, the external housing is pre-charged or pre-loaded with one or more target compounds.

In one embodiment, the devices of the subject invention contain a plurality of reservoirs that can be sequentially compromised, so as to release target compound in repeated doses over a period of time. This sequential release of target compound can recharge the external housing, as the target compound is integrated therein, so that it can continuously diffuse or volatilize sufficient insect repellent. When configured with an optimal arrangement of external housing materials, target compounds, triggering compounds, permeable cover openings, and container, the devices of the subject invention can provide significant insect repellency for an extended period of time.

When a device, according to the subject invention, is first deployed, there can be an initial "burst" release of target compound. This is especially noticeable with embodiments having a pre-charged external housing. If the external housing is not pre-charged, then a phenomenon such as that shown in FIGS. 12A, 12B and 12C might be observed, where the release rate increases over time until the external housing is saturated and then levels off to an approximately zero order release rate. Such phenomena are not uncommon and are often observed with devices that are saturated with volatile materials. Most often this burst release is caused by the initial dissipation or release of compound that has accumulated on the surface of the device. As the surface substance material diffuses or is volatilized, substance integrated within the device material migrates to the surface and is released or dissipated. Over time, the substance migration rates slowly taper off and provide what is commonly known as a "first-order" release rate, an example of which is shown in FIG. 5.

One of the advantages of the embodiments of the subject invention is that there can be provided a substantially constant concentration of a target substance that can be integrated into the external housing. By timing the release of target compound from the reservoirs, the external housing can realize a substantially constant level of saturation of such target substance. So, while a device of the subject invention may experience an initial burst effect upon initial deployment, the timed-release of compound from one or more reservoirs within the external housing inhibits the first-order release effect by re-saturating or re-charging the external housing, such that the external housing embodiments of the subject invention maintain a relatively constant saturation level. A permeable cover utilized in conjunction with an external housing experiencing relatively constant saturation level can provide a substantially zero-order release of target compound into a 3-dimensional spatial area around the device. More significantly, this zero order release rate can be maintained over a significant period of time.

The target compounds that can be utilized with the embodiments of the subject invention can comprise any of a variety of one or more substances or materials. It can be preferable for one or more of the target compounds to have a high volatility for better dispersal. However, the embodiments of the subject invention can also be utilized with low volatility compounds. A target compound can include any of a variety of one or more perfumes, fragrance oils or chemicals, deodorizers, disinfectants, or other substances desired to be dispersed or volatilized within or around an area.

Specific embodiments of the devices of the subject invention are utilized with target compounds comprising one or more repellents, as defined above. A variety of repellent compounds are known in the art and the choice of such compound can depend upon the target pest.

Some examples of compounds commonly used as repellents and/or pesticides are essential oils, such as almond bitter oil, anise oil, basil oil, bay oil, caraway oil, cardamom oil, celery oil, chamomile oil, cinnamon leaf oil, citronella oil, coriander oil, cumin oil, dill oil, *eucalyptus* oil, fennel oil, ginger oil, geraniol, grapefruit oil, lemongrass, lemon oil, lime oil, parsley oil, rose oil, spearmint oil (menthol), sweet orange oil, thyme oil, turmeric oil, and oil of wintergreen (also known as *Gaultheria* oil).

While the embodiments of the subject invention are amenable for use with any of a variety of target compounds, they are most advantageous because they can be utilized effectively with target compounds that are considered "demonstrably safe for the intended use" by the Environmental Protection Agency (EPA). More specifically, the embodiments of the subject invention can be utilized with those compounds or ingredients included on the Federal Insecticide, Fungicide, and Rodenticide Act (FIFRA) Section 25(b) Minimum Risk Pesticides listing. This list includes, but is not limited to, cedar oil, citronella oil, clove oil, geranium oil, lemongrass oil, linseed oil, mint oil, peppermint oil, rosemary oil, sodium chloride, white pepper, as well as other substances. If intended for human use, target compounds Generally Regarded As Safe (GRAS) by the Food and Drug Administration (FDA) can be utilized. A person skilled in the art would be able to determine any number of compounds that can be utilized with various embodiments of the subject invention. Such variations in target compounds are within the scope of the subject invention.

To be effective as a spatial repellent, a target compound needs to be adequately dispersed within a 3-dimensional area. While the volatility of the target compound can affect dispersal, the amount of surface area from which the target compound can disperse is also a factor. The concentration of the dispersed target compound is also a determining factor in how effective it will be for its intended purpose. For most repellents, there is a minimum threshold level that must be achieved for effective insect control. Many dispersal mechanisms require dilution of the target compound to facilitate storage and/or dispersal, which often makes it more difficult to achieve the required effective threshold, or requires more of the diluted product to be released, so that an effective amount of the target compound is vaporized.

The different embodiments of the subject invention have the ability to provide a variety of release rates, which can provide sufficient target compound for different environments. As will be discussed below, certain embodiments disclosed herein can provide release rates of between approximately 1 mg/hr up to an amount of approximately 12 mg/hr. It will be understood by a person skilled in the art, that one of the factors that can dictate the amount of release rate for a given embodiment is the surface area of the device. More specifically, the available surface area from which target compound can be dispersed is an important factor in release rate for any given target compound. A skilled artisan having access to the subject disclosure would be able to determine which embodiment and size thereof would be appropriate for a given area and pest to be controlled in that area. Such variations are within the scope of this invention.

One embodiment of the subject invention can utilize an external housing 20, as a dispersal mechanism. In one embodiment, the external housing comprises one or more materials that can absorb or take up the target compound. This can include, but is not limited to, silicone, latex, various plastics, nylon, and rubber, formed into any of a variety of shapes, weaves, spun products, solid masses, monoliths, other formations and combinations thereof. It may also include natural wood products, such as paper or wood board, natural fiber products, such as cotton, linen, flax, or hemp, as well as ceramics, glass, clay, charcoal, or any combinations thereof, and other materials suitable for use with embodiments of the subject invention. In a specific embodiment, the one or more materials of the external housing absorb the target compound in liquid form, while simultaneously allowing it to evaporate or disperse from the available surface area. It can be efficacious for the size, shape, and/or material of the external housing to benefit dispersal of the volatile compound. In one embodiment, the external housing absorbs a sufficient amount of target material, so that the levels dispersed from the available surface of the external housing provide an effective or desirable threshold amount within a pre-defined 3-dimensional area. In tests, it has been shown that devices utilizing a monolithic external housing with a total surface area of about 8 cubic inches can have a release rate of approximately 1-2 mg/hr and can continue to release at that approximate rate for 7-10 days after being deployed, depending upon the target compound.

One embodiment of subject invention utilizes an external housing 20 comprised of a latex rubber monolith. Latex rubber has several advantages for use with the subject invention. One particular advantage is its characterization as a material considered "demonstrably safe for the intended use" by the Environmental Protection Agency (EPA). More specifically, latex rubber is listed by the Federal Insecticide, Fungicide, and Rodenticide Act (FIFRA) Section 25(b) as a permitted inert material, implying a history of safe use under reasonable circumstances. A further advantage is the ability of latex rubber to readily absorb a variety of oils, both organic and organically-derived, and volatile substances and to facilitate their dispersal. A specific advantage is the ability of latex rubber to absorb citronella oil.

The absorptive capacity of latex rubber is also high compared to other materials. Latex materials can have high absorptive properties. This quality of latex rubber, in particular, allows the embodiments of the subject invention to be utilized with substantially pure target compound or active ingredient. Because the target ingredient does not have to be diluted in order to be absorbed, purer target ingredient can be diffused and can increase the effectiveness of the devices. However, it will be understood that a person with skill in the art would be able to determine a variety of materials that would be suitable for use as an external housing of the subject invention, including materials that would absorb citronella oil or other desirable target compound. Such variations in materials that provide the same function, in substantially the same way, with substantially the same result are within the scope of the subject invention.

In one embodiment, an external housing 20 sheet is formed of latex rubber with one or more internal chambers 30. FIGS. 1A, 2A, and 3A illustrate non-limiting examples of external housing embodiments having one or more internal chambers. In a further embodiment, the external housing can be reinforced with one or more materials that provide strength to the latex rubber. Such reinforcement materials can provide rigidity to the external housing, such that the shape or configuration of the external housing cannot be easily altered. Alternatively, the reinforcement material can allow the latex rubber material to flex, stretch, or bend in one or more directions.

An alternative embodiment utilizes a thin layer latex sheath as an external housing 20, such that the inside of the sheath forms an internal chamber 30. One or more reservoirs can be placed into the sheath and the sheath opening 23 can be closed with any suitable seal 45 to prevent leakage. When the one or more reservoirs are broken, the target compound 65 will release into the internal chamber 30, as illustrated in FIG. 14. The latex sheath housing is capable of absorbing and dispersing the target compound, similarly to the latex monoliths described above. Such devices have the advantage of providing an increased release rate of target material. For example, a thin layer latex device having about 9 cubic inches of surface area in contact with a target compound can release approximately 8 mg/hr of citronella oil.

In one embodiment, the latex rubber is reinforced with a woven material. In a more specific embodiment, the latex rubber is reinforced with a woven material that is a cotton gauze. However, the reinforcement material does not have to be woven and could comprise a multitude of other types of materials in addition to, or instead of, cotton, such as, for example, metal, nylon, plastic, glass, ceramics, wood products, animal products, silicone, or combinations thereof. It would be within the skill of a person trained in the art to determine an appropriate reinforcement material and configuration. Such modifications are within the scope of the subject invention.

Figure 10:
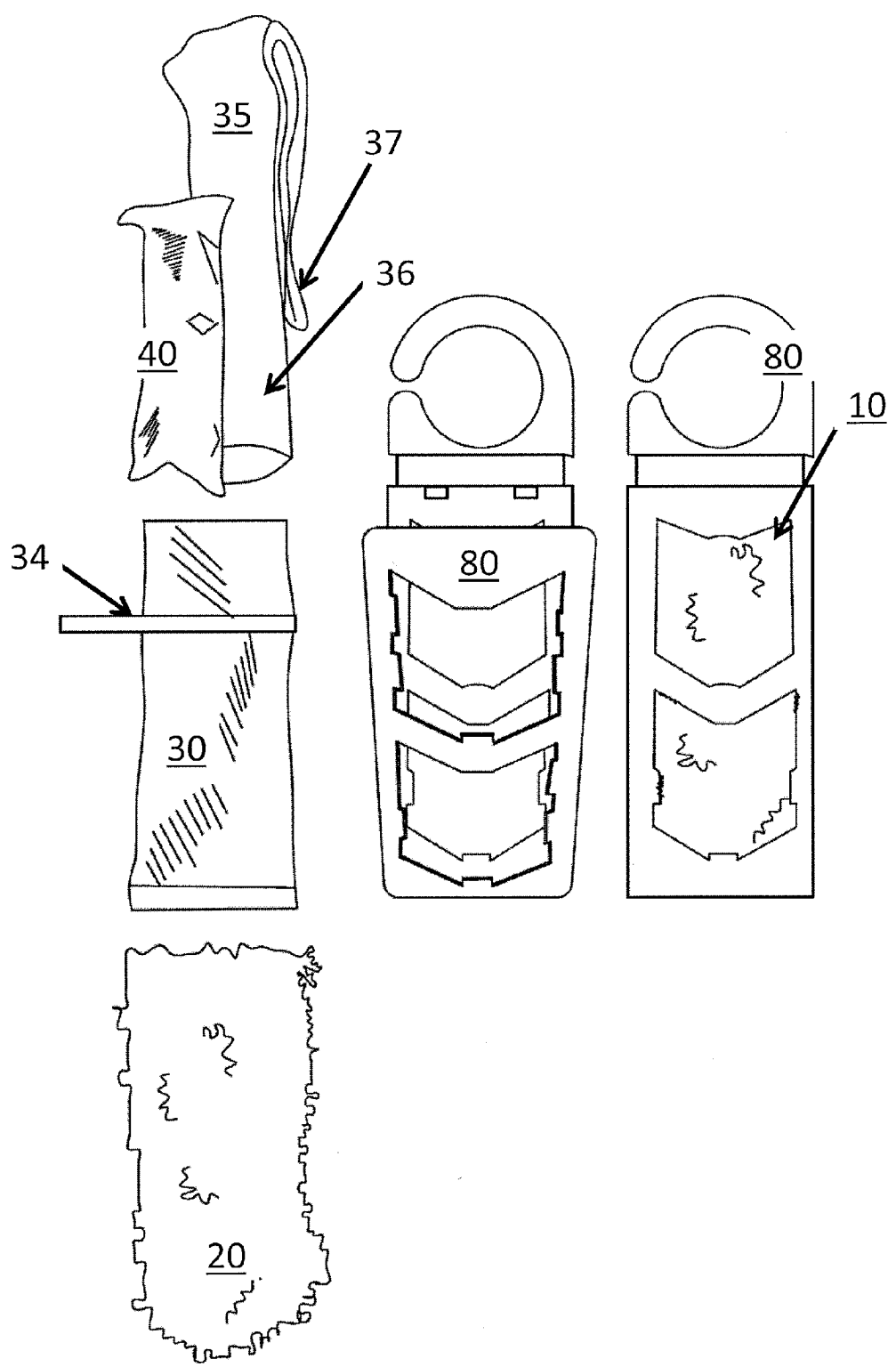
FIG. 10 is a photograph of an alternative embodiment of the subject invention utilizing a wick component surrounding a semi-permeable membrane reservoir containing target compound. On the left side of the figure are the components of the device and the far right side shows one example of the device after being assembled.

In an alternative embodiment, illustrated by way of example, in FIGS. 10 and 11, the external housing 20 can be formed of a flexible cloth or cloth-like material capable of rapid absorption and dispersal of volatile compounds. In a specific example, illustrated in FIGS. 10 and 11, the external housing can be a cotton-containing terry cloth material. In a further specific embodiment, the external housing is a sponge or sponge-like material through which target compound can migrate or disperse. In a further embodiment, the external housing is operatively connected to a wick 35 that extends from a mouth 33 of the internal chamber 30 to make contact with the external housing 20. With this embodiment, the wick 35 is the mechanism by which the external housing is replenished with target compound released within the internal chamber.

In one embodiment, the wick and the external housing are separate components that are in operable contact. For example, the wick and external housing can be placed so that they touch or make contact with each other. By way of further non-limiting example, the delivering end 37 of a wick can actually be attached or connected to the external housing by another device or technique. It can be sewn, clamped, banded, constricted, stapled, adhered, heat sealed, pressure sealed, crimped, melded, molded, or some combination thereof, to the housing. Alternatively, the wick and the external housing can be formed as a single component or article, such that the wick is not required to be additionally connected to the external housing.

FIG. 11 illustrates one embodiment of the subject invention where the external housing 20 is formed as a sleeve of material into which an impermeable internal chamber 30 can be placed. A wick 35 can have receiving end 36 further placed within the internal chamber and, if necessary, around or in close proximity to a reservoir. The reservoir can also be of an impermeable, but frangible material that can be popped, ruptured, cracked, broken, ripped, or otherwise mechanically compromised to create at least one opening therein for release of target compound. Alternatively, one or more of the reservoirs can be degradable, by methods or techniques described herein. In FIG. 11, the receiving end of a wick is shown to form a seat into which the reservoir can be placed. But, other configurations or arrangements can be utilized as well. Ideally, the wick is configured and arranged within an internal chamber so that all or most of the available target compound can be absorbed by the receiving end 36 and carried through the wick to the outer housing 20. Thus, the wick is not fully contained within the internal chamber, but can have a delivering end 37 that extends through the mouth 33 in the internal chamber, so that the target compound can be, for example, leached by the wick to the outside of the internal chamber.

There can also be a narrowing apparatus 34 at or near the mouth 33 that reduces the size of the mouth relative to the rest of the internal chamber. FIG. 11 illustrates a further embodiment wherein the mouth in the internal chamber has a narrowing apparatus that can be used around the mouth 33 so that it is reduced, constricted, or tightened around the wick that extends therefrom. In this example, the narrowing apparatus is a "zip-tie" device. Other devices and mechanism that can be used to reduce, constrict, or tighten the mouth around the wick have been recited above with regard to connecting the wick to the external housing and are reiterated here with regard to reducing the mouth.

Once the wick 35 and reservoir 40 have been sealed into the internal chamber 30, the internal chamber can be placed into an external housing 20 of absorbent, flexible material, as described above. The external housing can also have an access 23. The wick can be placed in contact with the sleeve material of the external housing to ensure that target compound in and/or on the wick is carried to and absorbed by or otherwise distributed through all or most of the sleeve. The access in the sleeve can be sealed to maintain the internal chamber therein, by the same or different devices and techniques as used to seal the internal chamber. However, the sleeve does not have to sealed and can be left open. In the example shown in FIG. 11, the assembled external housing is placed into a container 80. Thus, if desired, the sleeve end with the access 23 could be left open or folded over prior to placement in the container. Tests have shown that embodiments of these devices, which utilize a wick, having dimensions of about 3"×1" can provide a release rate of approximately 10-12 mg/hr and continue to provide that release rate for 7-14 days, depending upon the target compound.

The amount of target ingredient carried or transferred to the external housing by the wick can depend upon the size of the mouth relative to the diameter of the wick. It is well known to skilled artisans that the rate of capillary action depends, at least in part, on the viscosity of the liquid moving through the fibers of a material and the amount of space between the fibers of the material. A constriction of the wick can be used to control the amount of target compound that moves through the material of a wick.

In one embodiment, the mouth 33 of the internal chamber, can be used to create a constriction in the wick. Alternatively, a constriction can be formed in the wick by other methods or devices. For example, the same techniques used to constrict the mouth could also be used in another part of the wick to create a constriction 38. Because the constriction can limit the amount of target compound that moves through the wick material, a constriction can be most effective if employed at a portion of the wick that is not in direct contact with the target compound. Otherwise, the constriction may not be effective, as the target compound can be absorbed from either side of the constriction. FIG. 15 illustrates an embodiment where a constriction 38 is formed in a portion of the wick that is outside of the internal chamber 30.

The purpose of the internal chamber 30 within the external housing 20 is to compartmentalize at least one reservoir. Because certain embodiments employ an external chamber of one or more materials capable of absorbing the target ingredient, it would not be feasible to dispose the target ingredient directly into the internal chamber without some method or device for preventing its absorption until the desired time. Thus, triggering compound 65 or target compound 75 can be stored within a reservoir 40. Certain embodiments further require the integrity of one or more of the reservoirs to be damaged or compromised, so as to release target compound or triggering compound. In one embodiment, that part of the external housing 20 that forms the internal chamber 30 is sufficiently flexible to allow mechanical rupturing of at least one reservoir.

A variety of materials can be utilized for a reservoir including, but not limited to, glass, ceramics, plastics, nylon, wood, natural fibers or plant products, gelatin, cellulose, hydroxyl methyl cellulose, silicone, polyethylene, aluminized polyethylene, polymers, and/or combinations thereof. While not required, it can be preferable to employ inert materials for a reservoir. More particularly, it can be beneficial if the reservoir material is selected from one or more of the inert materials on the FIFRA 25(b) list, which is mentioned above. If intended for human use, target compounds Generally Regarded As Safe (GRAS) by the Food and Drug Administration (FDA) can be utilized. It is within the skill of a person trained in the art, having benefit of the subject disclosure, to determine a variety of materials that would be appropriate for the type of reservoir(s) utilized with embodiments of the subject invention. Such variations that perform the same function, in substantially the same way, with substantially the same results, are within the scope of the subject invention. A reservoir 40 of the subject invention can be configured in several ways. In one embodiment, the internal chamber 20 is lined with a material that prevents absorption of a compound. Such lining material 42 can be formed as part of, or can be operably attached to, the material of the external housing that forms the internal chamber. In one embodiment, the lining material 42 can be mechanically or physically cracked and/or dislodged from the internal chamber by squeezing, crushing, crimping, or otherwise deforming the external housing 20 formed around the internal chamber. In this way, any compound isolated by the lining material can be provided access to the external housing and/or other reservoirs.

In an alternative embodiment, a reservoir 40 is a separate container, capsule, ampoule, or other bulbous vessel, such as illustrated, for example, in FIGS. 10 and 11, that resides in the internal chamber 30. In one embodiment, a container reservoir 44 is similar to a reservoir of lining material 22 in that, when the external housing 20 is deformed, the container reservoir 44 can be physically or mechanically cracked, popped, ruptured, or otherwise damaged or compromised to release compound within.

The ability of the subject invention to provide a near zero-order, long-term release rate of target compound can be facilitated by the sequential release of pre-determined amounts of target compound within the internal chamber. The sequential release allows the target compound to be absorbed by the external housing, in effect, periodically recharging the external housing. This can ensure that the amount of target material evaporated from the surface of the external housing remains generally constant and provides effective levels within a spatial area. The sequential release of target compound can be accomplished by providing multiple reservoirs of target compound that can be compromised in some sequential order.

In an alternative embodiment, a reservoir 40 comprises a material that can be chemically degraded, fragmented, ruptured, dissolved, solvated, or otherwise materially-compromised by methods other than mechanical deforming means. By way of non-limiting example, a reservoir can comprise a gelatin or cellulose material that dissolves or otherwise ruptures when exposed to water, target material, or other substance. By way of further non-limiting example, a reservoir can comprise a polystyrene or plastic material that dissolves or ruptures in the presence of certain triggering substances. In a further embodiment, such a chemically-active reservoir 46 can be configured to chemically degrade at different time points. By way of non-limiting example, a chemically-active reservoir could be configured with various thicknesses, one or more layers of different degradable materials, materials that degrade at a measurable rate in the presence of certain types of substances, or by other means that may be known to those with skill in the art. Reservoirs can also be layered or placed in specific locations within the internal chamber, so that their rate of degradation is controlled by proximity. In another embodiment, there can be more than one internal chamber, such as in the example shown in FIG. 2B, such that reservoirs can be placed within multiple internal chambers 30 to control their rate of release of target or active compounds.

When target compound is released from a reservoir, it flows or migrates towards the walls of the internal chamber, so that it can be absorbed into the external housing. As the different reservoirs release their target compound at pre-determined or at least sequential intervals, the external housing can be repeatedly replenished or re-saturated. This continual replenishment or re-saturation can allow the target compound to be diffused at a constant rate and, thus, maintained at specific levels within a spatial area. Ideally, the reservoirs can release their target compound at intervals that cause the release rate from the external housing to mimic a zero-order release rate. Thus, in a particular embodiment, when the concentration within the external housing begins to wane below a certain threshold, another reservoir will be ready to rupture and release target compound that will replenish the concentration within the external housing, so that the release rate does not approach zero and, preferably, does not fall below an effective level.

In one embodiment, a target compound can also act as a triggering compound, such that when released, it can degrade or compromise other reservoirs to mitigate release of their target compounds. In a further embodiment, multiple reservoirs 40 within the internal chamber 30 can comprise different materials and contain different compounds. Rupturing the reservoirs in a specific order can initiate a chain-reaction of sequential releases of target and/or triggering compounds from various reservoirs. Still further, both mechanical and chemical methods can be used to compromise reservoirs.

In one embodiment, illustrated by way of example in FIGS. 1B and 2B, a first reservoir 47A containing an initial triggering compound, such as, for example, water or isopropyl alcohol, can be mechanically ruptured by deforming the external housing. Once released, the triggering compound can contact a second reservoir 47B and begin dissolving or otherwise degrading the integrity of that second reservoir. Eventually, the second reservoir will release target compound, which will flow out and towards the external housing to be absorbed, while at the same time effecting degradation of a third reservoir 47C. The third reservoir can contain the same compound as the first reservoir, i.e., water, for example, such that when released from its degraded reservoir, it can act on a fourth reservoir 47D containing more target compound. Alternatively, the third reservoir can contain more target compound, such that when released from its degraded reservoir, it replenishes the external housing, while simultaneously acting to degrade a fourth, target compound-containing, reservoir. In this way, the release of triggering and target compounds can continue until all of the reservoirs have been ruptured.

FIG. 1B illustrates an embodiment wherein the reservoirs are contained within a single internal chamber. The reservoirs can be ruptured as described above. But, to facilitate the sequential release of compounds, the reservoirs can be modified so that even when contacted with triggering or target compound, they can each rupture at different times. In one embodiment, the reservoirs comprise materials of different thicknesses, so that thinner walled reservoirs will rupture before thicker walled reservoirs, even if both are contacted with target or triggering compound at the same time. In still another embodiment, the reservoirs are arranged within one or more internal chambers in a specific configuration that encourages sequential rupturing of reservoirs and timed-release of target compound.

It can be seen from the above description that one or more target materials and/or triggering materials are isolated within an internal chamber. This method of operation provides a unique and very advantageous feature to the embodiments of the subject invention, in that, it allows for the use of pure or almost pure target compound. Many devices utilized to repel insects have storage and/or delivery systems that require the target compound to be mixed with various other products, such as, by way of example, binders, carriers, aerosol compounds, stabilizers, etc., to protect the target compound for storage and/or utilize the target compound with the device. The embodiments of the subject invention provide the advantage of being able to utilize substantially pure target compound because the method of storage can maintain the life of the target compound without additives and the device utilized for dispersal is more effective if it can uptake pure target compound, especially oil-based compounds like citronella oil.

Another factor addressed by the embodiments of the subject invention is the rate of evaporation of target material from the external housing 20. FIG. 5, mentioned above, illustrates a typical first-order release rate that may be experienced by an external housing of the subject invention, comprising just a polymer material, which has been initially saturated with a target compound. In this specific example, the target compound utilized can be citronella oil and the external housing can be comprised of latex rubber. When the external housing is left exposed, there is an initial high release rate, but the citronella oil diffuses or volatilizes at a constant rate until it reaches zero release. Often, before the citronella oil is fully diffused, it ceases to release an effective repellent amount. Thus, any remaining repellent released after that time can be essentially wasted.

As described previously, embodiments of the subject invention are effective in recharging the external housing at intervals that can ensure an effective amount of target compound is continually released from the external housing. However, each time the external housing is replenished, there can be an initial burst release of material and then a relatively rapid decline in release rate, similar to that shown in FIG. 5. The subject invention is able to control the amount of target material released from the external housing, such that only an effective amount of material is released and the initial burst effect observed with replenishment is inhibited.

In one embodiment, the external housing 20 is sealed within a permeable cover 50. The material of the permeable cover can be impervious to the target compound. In a further embodiment, the permeable cover has one or more openings 52 that allow target material to pass through. The number and arrangement of openings can vary depending upon the size of the external housing, the volatility of the target material, susceptibility to blockage, the diameter or area of the openings, environmental factors, and other factors that would be understood by a person skilled in the art. The permeable cover preferably provides openings that expose sufficient surface area of the external housing to prevent pooling or concentration of target material in one or more areas. In other words, the permeable cover allows target material to be released in a relatively constant manner from the effective surface of the external housing. However, depending upon materials utilized, it can be preferable for target material to concentrate in specified areas of the external housing. An alternative embodiment of the permeable covering has openings configured to concentrate target material in or around the external housing and allow release through openings in other areas around the external housing. This can be achieved by altering the size of the openings such that smaller openings in one area release less material than larger openings in another area of the permeable cover. Alternatively, certain areas of the permeable cover can be without openings, such that no target material can be released. FIG. 4B illustrates an example surface of a permeable cover having areas with no openings 52A, areas with relatively small openings 52B, and areas with larger openings 53C or openings of specific shape 53D for controlling release rates.

A permeable covering 50 can comprise any number of one or more materials and the choice of material will depend upon a plurality of factors. In one embodiment, the permeable cover is a sheet material that is formed around and maintained in close proximity to the external housing. FIG. 4A illustrates one embodiment of a permeable cover in the form of a sleeve into which an external housing can be inserted and sealed to form a tight fit around the external housing. Non-limiting examples of material that can be used for this embodiment are polyvinyl chloride (PVC) or low density polyethylene (LDPE), commercially known as Saran™ Wrap. Polyethylene is a material considered "demonstrably safe for the intended use" by the EPA on the FIFRA 25(b) list. Another example of a material that can be utilized to provide a shape-conforming permeable cover is polyolefin, often referred to as "shrink wrap." A person skilled in the art, having benefit of the subject disclosure, can determine which of one or more known materials would be suitable for use with a specific embodiment. Such variations are within the scope of the subject invention.

Figure 6:
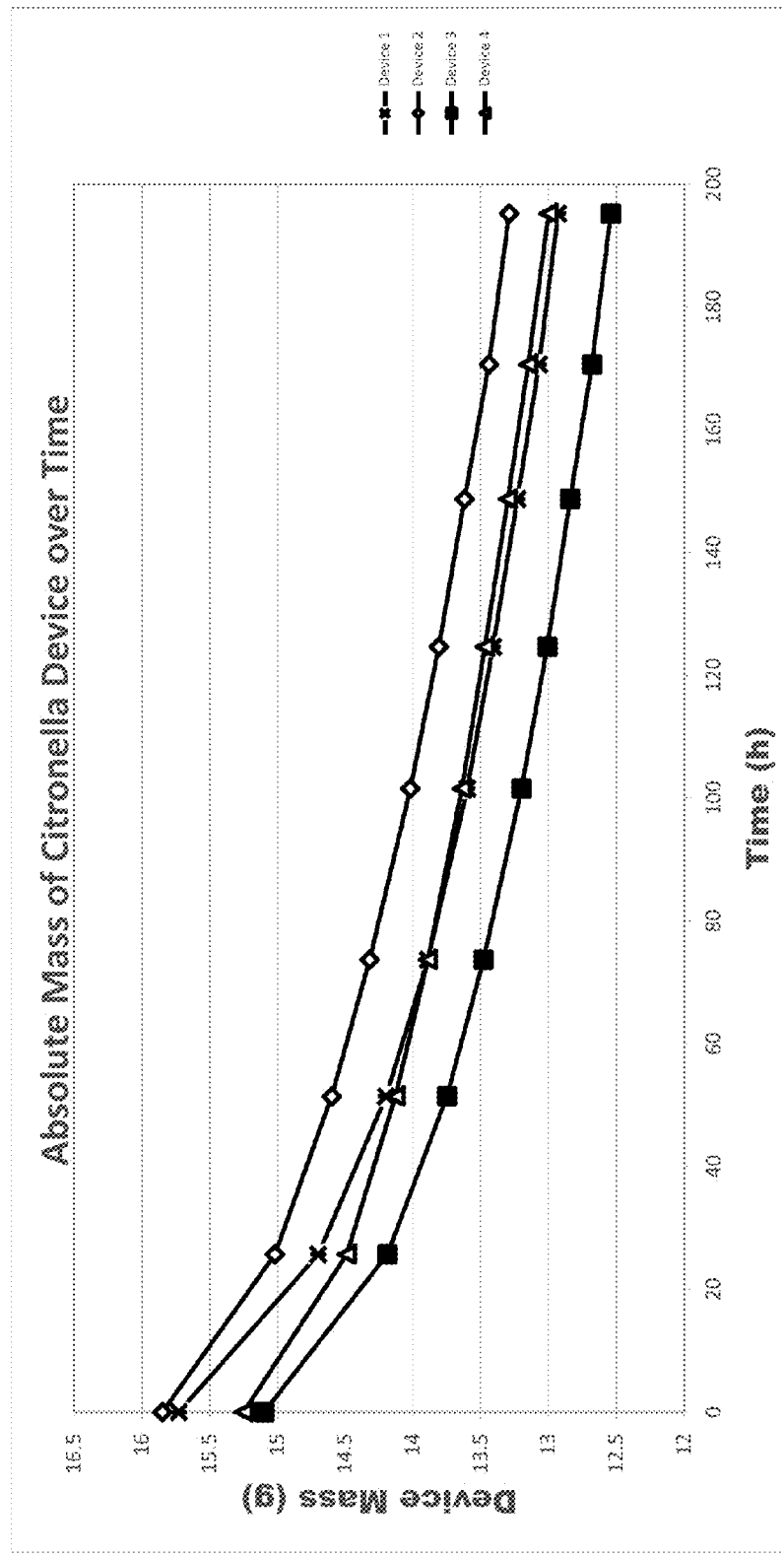
FIG. 6 is a graph illustrating the absolute mass over time of four embodiments of the devices of the subject invention utilizing citronella oil as the target compound. It can be seen in this graph that while the mass of the device experiences an initial decrease, the loss in mass is slowed over time, indicating that the amount of the citronella oil being released is more controlled and at 200 hours of use the target compound is still being volatilized.
Figure 7:
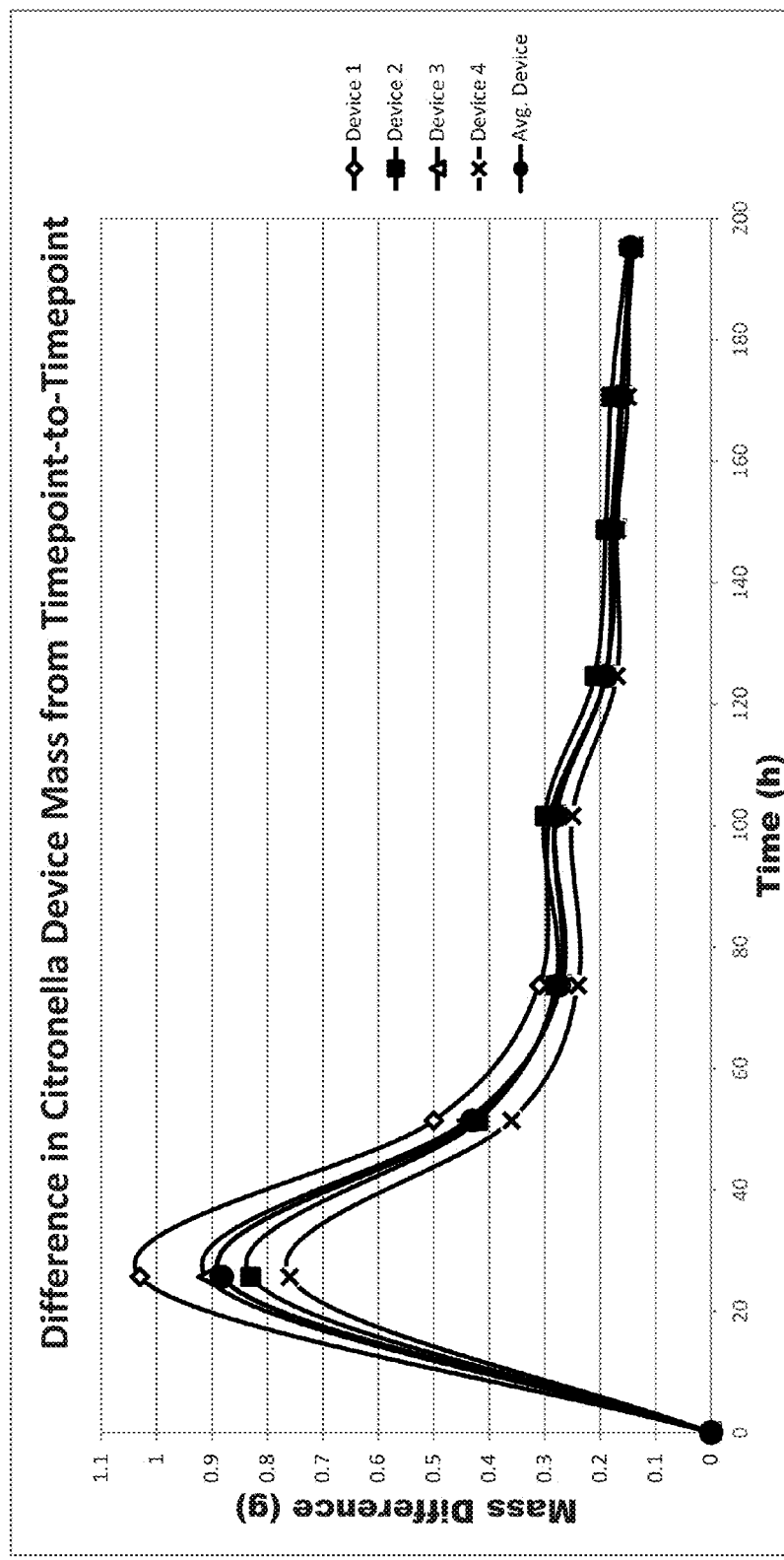
FIG. 7 is a graph illustrating the difference in mass over time of four embodiments of the devices of the subject invention utilizing citronella as a target compound. This graph shows that there is an initial, relatively large decrease, i.e., release, of the active ingredient, when the device is first activated. Within 60 hours after activation, the devices begin to release an effective and more stabilized amount of the active ingredient. At 200 hours after activation, it can be seen that the devices were still able to release an effective amount of the active ingredient.
Figure 12A:
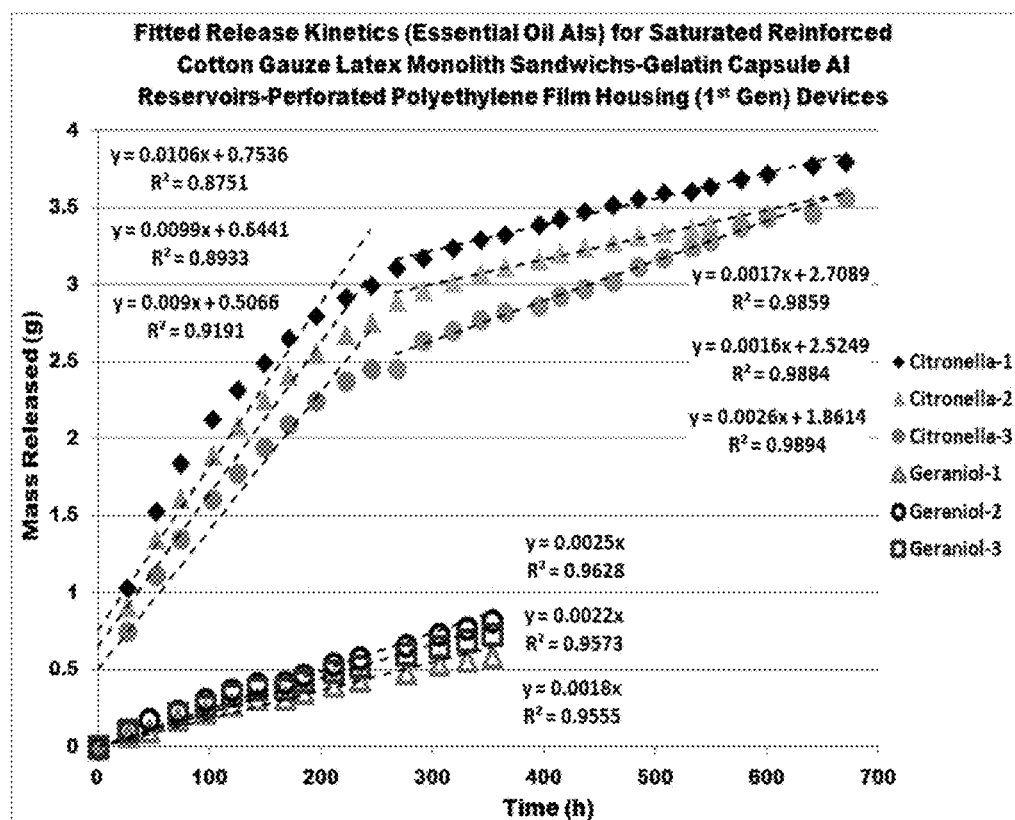
FIG. 12A shows a graph of the release kinetics data of active ingredient (a.k.a., target compound) from an embodiment that includes one or more cotton gauze reinforced latex monolith sandwiches (containing a gelatin reservoir) covered with perforated polyethylene film saturated with active ingredient. (Note: Slopes from the fitted regression lines are taken as the apparent release rate.)
Figure 12B:
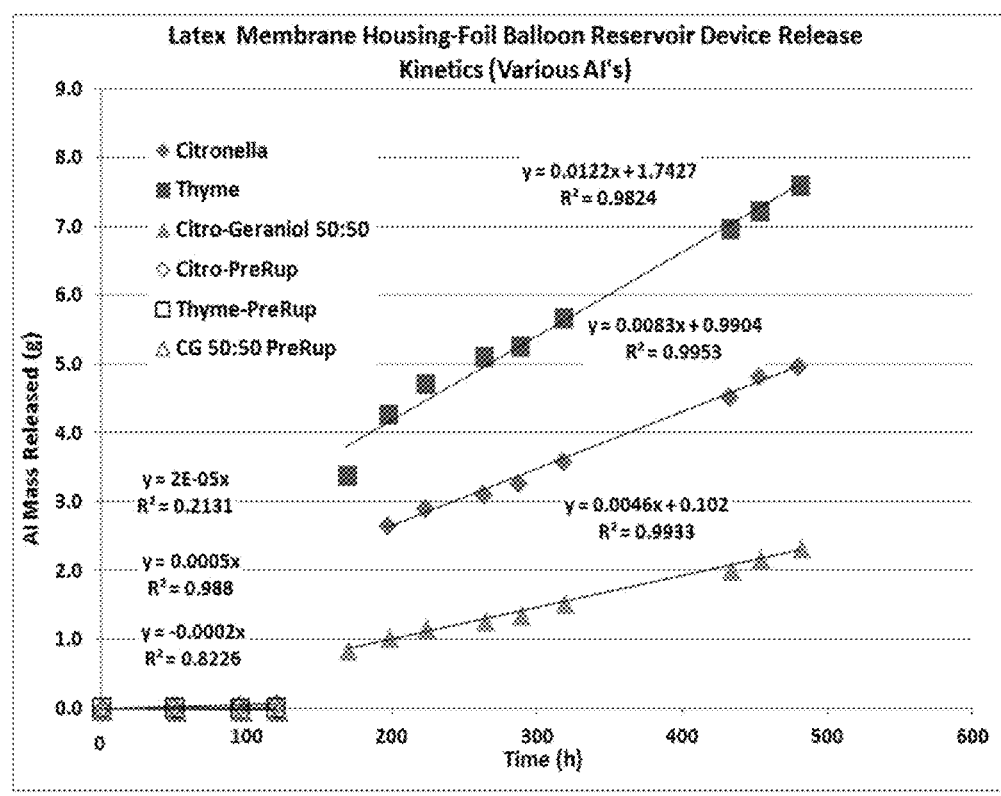
FIG. 12B shows a graph of the release kinetics data for various active ingredients (a.k.a., target compound) from an embodiment that utilizes a latex membrane-polyethylene film reservoir(s). (Note: Slopes from the fitted regression lines are taken as the apparent release rate.)
Figure 12C:
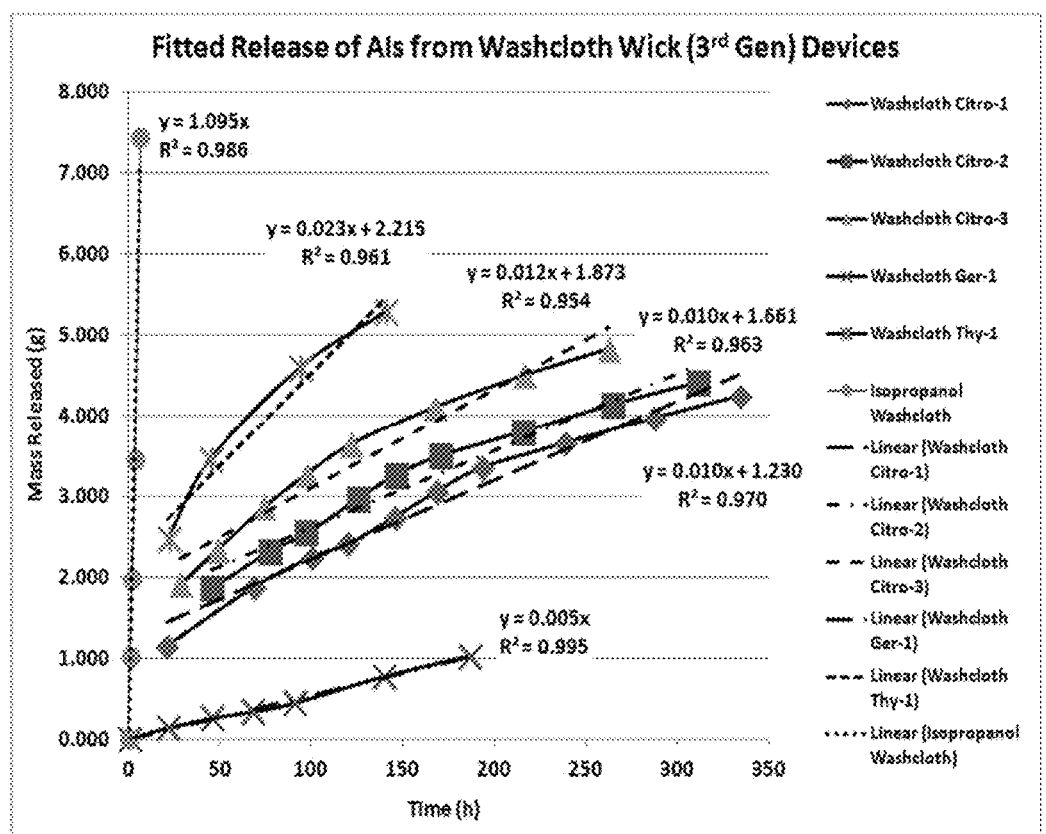
FIG. 12C shows a graph of the release kinetics data for various active ingredients (a.k.a., target compound) from a wick-based embodiment. (Note: Slopes from the fitted regression lines are taken as the apparent release rate.)
Figure 13:
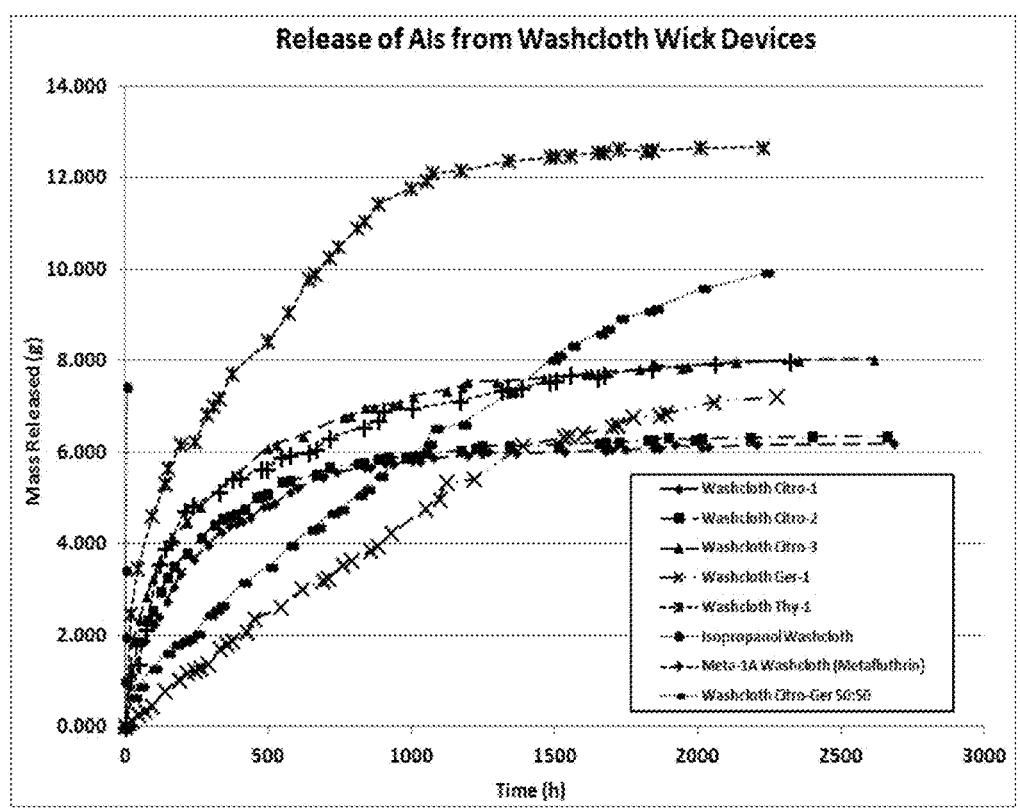
FIG. 13 is a graph of the release kinetics for embodiments utilizing wicks of various materials.

By utilizing a permeable cover, the amount of material released from the surface of the external housing is more controlled. Thus, the concentration of target material absorbed by the external housing can have little or no effect on the amount of target material released into a spatial area. When a permeable covering is utilized in conjunction with a sequential target compound release method, such as described above, the external housing is able to release a more constant amount of target material and, as demonstrated in FIGS. 6, 7, and 12A, provide an effective amount for a longer period of time.

When utilized in a confined or enclosed space, it is possible for the target substance being released to become concentrated within that space. Even with a zero-order release rate, a constant release of target substance can result in undesirable or unnecessary concentration levels in confined areas. Thus, it can be beneficial for the amount of material released through the permeable cover to be controllable or regulated, so as to prevent over-concentration of target substance. One embodiment of the subject invention employs a regulator 70 that can be used over the permeable cover to block some portions of the surface area of the permeable cover 50 and reduce the amount of target compound being released. Ideally, the use of a regulator will not affect the zero-order release rate, but will control the amount of target material being released at a zero-order rate.

Figure 4A:
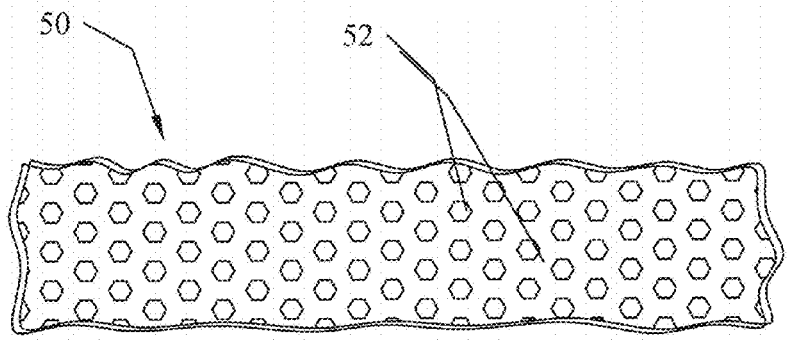
FIG. 4A illustrates one example of a permeable covering that can be utilized with a release device of the subject invention.
Figure 4B:
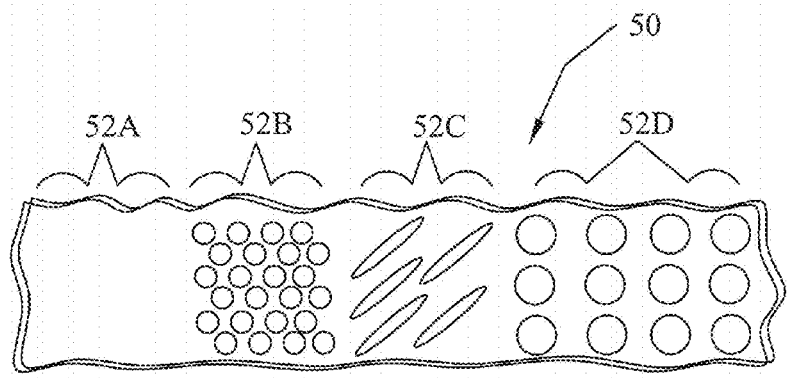
FIG. 4B illustrates examples of different types of permeable covering material, including areas of the material that have no perforations, different size perforations, or different shaped perforations. The number of perforations in each category can also vary.
Figure 4C:
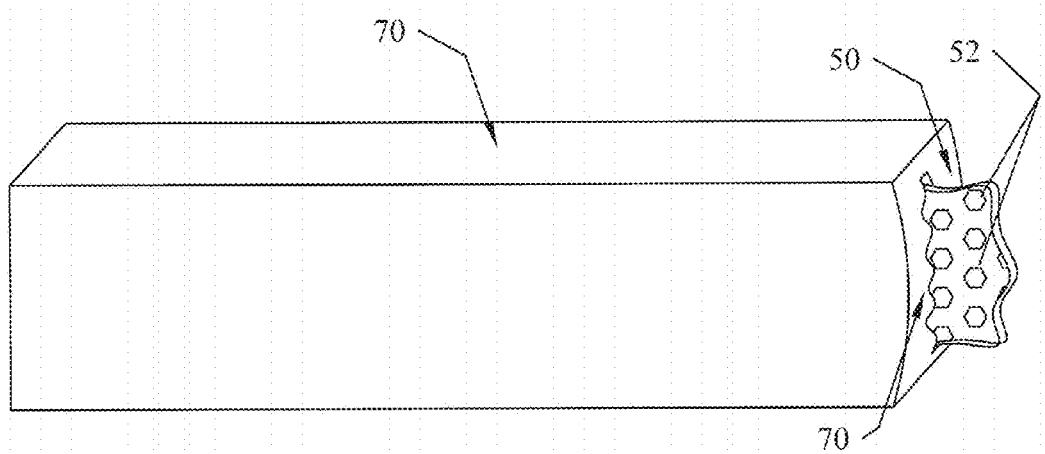
FIG. 4C illustrates one embodiment of a regulator, according to the subject invention. In this illustration, a release device with a permeable cover is shown extending partially from the opening in the regulator.

In one embodiment, a regulator comprises an impermeable material that prevents diffusion of target compound therethrough. A regulator can be a flexible or semi-flexible cover that simply pulls or slides over some part of the release device. This can be, by way of non-limiting example, a foil or cellulose acetate sleeve-like covering. Alternatively, the regulator can be a rigid covering. There can be a flexible or shape conforming diaphragm 72 in the regulator that allows passage of the release device therethrough, but which remains in close proximity to the release device to help contain target compound within the regulator. FIG. 4C shows an example of a regulator that can be utilized with a release device of the subject invention.

While the release devices 10 of the subject invention are effective as described above, it can be beneficial or desirable for the devices to be enclosed within a container. This can ensure that undesirable contact with the target compound is avoided. The container can also provide certain advantages with regard to where the release devices can be placed. A container device can also be designed to activate release devices of the subject invention.

In general a container 80 embodiment of the subject invention is a device of any desirable shape or configuration that has a space 82 therein or structural features for securing a release device of the subject invention. A container can have a multitude of characteristics, including, but not limited to, structures for holding or securing the container in a particular area, openings for air flow or release of target compound, secondary openings that allow removal and/or replacement of a release device, removable seals to prevent release of target compound, as well as ergonomic or decorative features.

Embodiments of the container can be configured to activate a release device of the subject invention. In further embodiments, the container can be utilized to mechanically compromise, as discussed above, one or more reservoirs within an internal chamber 30. In still further embodiments, the container can be utilized to initiate a sequential release sequence within the external housing 20.

FIGS. 10 and 11 illustrate a container embodiment often referred to as a "clam-shell" style, where two sides can be folded up to form an area or space between them. A release device 10 of the subject invention can be configured to be placed between the two sides of the clam-shell container. When the sides are folded up and secured, the release device 10 is within that area or space and the container sides, when brought together or in close proximity, will compress the one or more reservoirs inside the release device, compromising or rupturing the release device and releasing the target compound to activate the device. Alternatively, or in addition to, after the release device is secured in the container, additional pressure can be exerted on the sides of the container and/or the release device therein to release the target compound or encourage faster or greater release of the target compound.

Figure 2B:
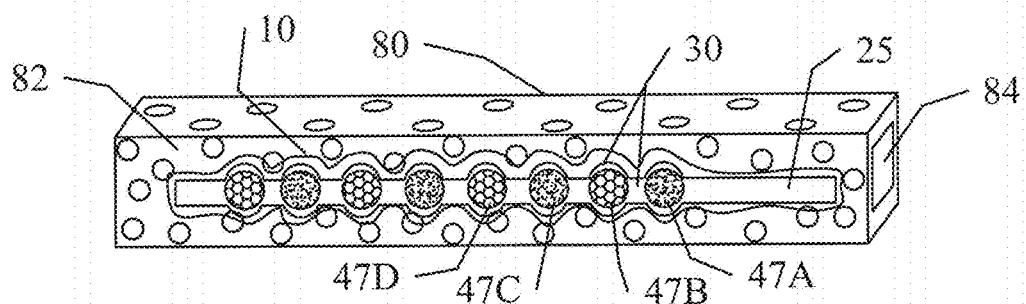
FIG. 2B is a side view of the embodiment in FIG. 2A showing how the multiple internal chambers can be connected, so that compounds within the reservoirs, when released, can contact reservoirs in adjacent internal chambers.
Figure 2C:
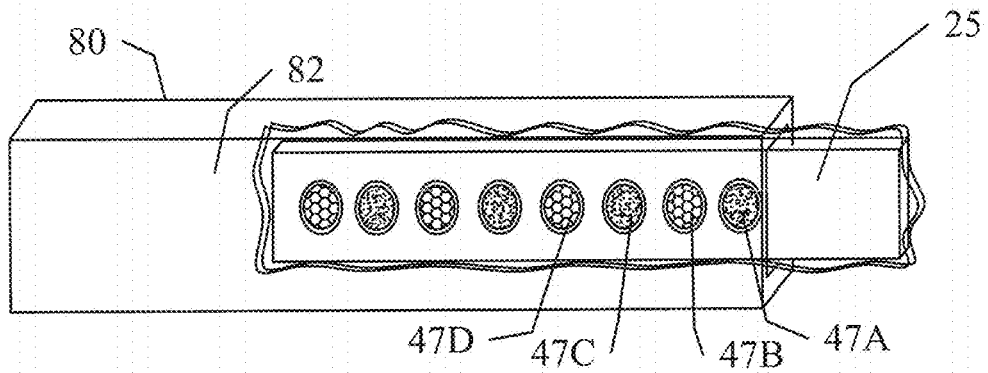
FIG. 2C shows an embodiment where a device of the subject invention is enclosed within a container and a tag end of the device can be pulled through an appropriately sized opening within the container. A reservoir within the external housing is inhibited from exiting the opening and can be used to rupture the reservoir.
Figure 2D:
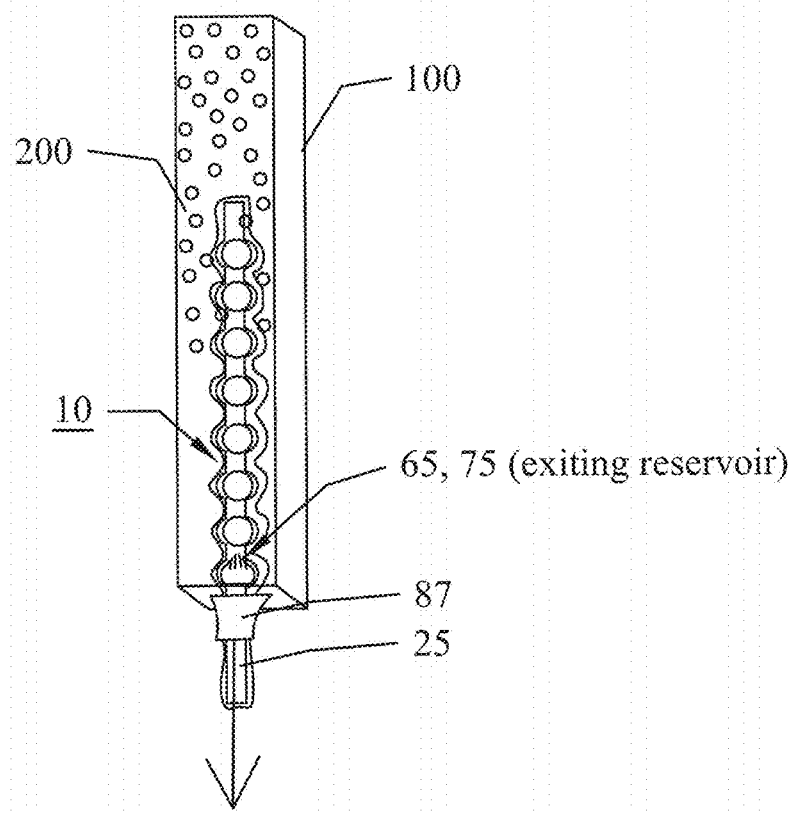
FIG. 2D shows an embodiment of a container having a funnel-shaped secondary opening for rupturing a reservoir upon exiting the container.
Figure 2E:
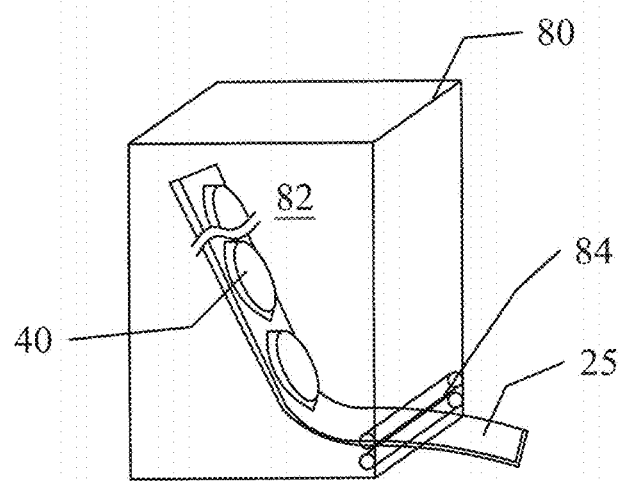
FIG. 2E shows an embodiment of a container with structures for rupturing a reservoir upon exiting the container.

In one embodiment, the container comprises a secondary opening 84 through which a tag end 25 of the external housing can be extracted. FIGS. 2A and 2B illustrate an embodiment of a release device 10 secured within a container 80. The dimensions of the secondary opening and/or the release device can be such that an internal chamber 30 within the external housing 20 is inhibited from passing through, or at least easily passing through, the secondary opening without being mechanically ruptured or compromised in such a way that the compound within is released. FIG. 2C shows an example of a container where the tag end 25 can be pulled through the secondary opening, but a reservoir 40 within the internal chamber is inhibited. The secondary opening can further be constructed, or have features or structures thereon that encourage rupturing of the reservoir, preferably without damage to the external housing. In a particular embodiment, the secondary opening has a funnel 87 shape that not only ruptures a reservoir, but can urge compound therein to flow away from the secondary opening and towards that portion of the external housing still in the container. FIGS. 2D and 2E illustrate non-limiting examples of such embodiments.

The factors that can be considered by those skilled in the art with regard to the choice of materials for each of the components of the subject invention have been discussed above and are reasserted here with regard to the container. In a particular embodiment, the container is comprised of a rigid material with sufficient durability to withstand normal use indoors or outdoors.

The release devices of the subject invention are amenable for use in numerous areas where it is desirable to control insects. They can be placed so as to control insects in a specified area, which can include rooms, tents, barracks, barns, sheds, stalls, vehicles, or other enclosed or semi-enclosed areas. A particular advantage of these devices is their ability to be useful over a long period of time. Thus, situations in which it may not be feasible to regularly monitor or replace a release device would particularly benefit from the devices of the subject invention. A further advantage is the ability of specific embodiments to utilize pure or substantially pure target compound, resulting in a relatively small volume of target compound being released in order to provide an effective dose within an area. This can further allow the release devices to be relatively compact.

A particular use for the embodiments of the subject invention is as an individual repellent system for humans or animals. The compactness of the devices allows them to be removably attached to clothing, animal equipment, or other personal devices within close proximity. This can allow the devices to be mobilized and, as a result, the spatial area of insect repellency to move with the individual. Specific embodiments can include a container 80 having a proximal side 100 that can be closed or sealed, so that target compound is not released directly against the individual. The distal side 200, or that side directed away from the individual, can have sufficient openings to compensate for the proximal side being unavailable to diffuse or volatilize material.

The following are examples that illustrate procedures for practicing the subject invention. The examples are provided for the purpose of illustration only and should not be construed as limiting. Thus, any and all variations that become evident as a result of the teachings herein or from the following examples are contemplated to be within the scope of the present invention.

EXAMPLE 1

Field Test of a Single Charge Volatile Insect Repellent Release Device Having First Order Release Rate Single charged release devices of the subject invention were field tested in Cedar Key, Fla. to determine the effectiveness in repelling insects from traps baited with dry ice as a $CO_2$ source. Initially, several release devices were prepared from a liquid latex rubber reinforced with commercially available cotton gauze according to standard techniques. Prepared devices approximately 3 in.×1 in.×⅛ in. were soaked in pure citronella oil until approximately 10 grams of oil was absorbed by each device. The saturated devices were subsequently wrapped in commercially available foil wrap for storage. It should be noted that these devices did not include a permeable cover. Thus, the devices provided a first-order release or dispersal rate of the citronella oil.

In field tests, a control trap was set and baited with sufficient dry ice to expel $CO_2$ for at least 3 hours. A test trap was also set and baited with sufficient dry ice to expel $CO_2$ for at least 3 hours and included 5 soaked release devices removed from the foil storage wrap and placed within the trap. The release devices were weighed before use; data are shown in Table 1.

The first field test was conducted on Apr. 19, 2013, which was noted to be a hot, windy day with high humidity. The control and test traps were set from 2 p.m. to 4:45 p.m. After completion of the testing period the individual release devices utilized in the test trap were weighed and wrapped again in commercially available foil wrap. Table 1 shows the resultant weight loss of each release device, which correlates to the amount of citronella oil dispersed by each device during the testing period.

TABLE 1

| Device # | Pre-test weight (grams) | Post-test weight (grams) | Weight Lost (grams) |
| --- | --- | --- | --- |
| #1 | 19.32 g | 17.93 g | 1.39 |
| #2 | 19.37 | 18.36 | 1.01 |
| #3 | 18.82 | 17.57 | 1.25 |
| #4 | 19.11 | 17.68 | 1.43 |
| #5 | 13.56 | 12.73 | 0.83 |

Wt loss (mainly citronella):
Total of all devices = 5.91 g over 2.75 hr (2.75 g/hr)
Average per device = 1.182 g over 2.75 hr (0.423 g/hr)

Analysis of the Trap Contents:
Citronella test trap: Insect ratio: control trap/test trap=256/5=51
    4 *Culicoides mississippiensis*
    1 *Anopheles crucians*
Control trap:
    225 *Culicoides mississippiensis*
    18 *Culicoides furens*
    8 "others"

A second trial was conducted in Cedar Key, Fla. in approximately the same location as the first test with the same traps utilized previously. Again, the control trap was set and baited with sufficient dry ice to expel $CO_2$ for at least 3 hours. The test trap was also set and baited with sufficient dry ice to expel $CO_2$ for at least 3 hours and included 5 soaked release devices within the trap.

The second field test was conducted on Apr. 23, 2013, between 1:45 p.m. and 3:45 p.m. This test was conducted to determine the effectiveness of the citronella soaked release devices.

Analysis of the Trap Contents Showed:
Citronella test trap: Insect ratio: control trap/test trap=4719/86=55
    86 *Culicoides mississippiensis*
Control test trap:
    4648 *Culicoides mississippiensis*
    71 "other" species The results show approximately a 98% reduction in insect presence, which indicates that citronella soaked devices are an effective control mechanism.

EXAMPLE 2

Field Test of Single Charge Volatile Insect Repellent Release Device Configured for Temporary Zero-Order Release Rate Single charged release devices of the subject invention were field tested in stairwells of an apartment complex in Gainesville, Fla. to determine the effectiveness of the device and of repellent compositions for repelling insects, particularly *Culex quinquefasciatus* mosquitoes. This insect is known to rest within the dead airspace of stairwells, such as the one shown in FIG. 8. Initially, release devices were prepared from a liquid latex rubber reinforced with commercially available cotton gauze according to standard techniques. The devices were approximately 3 in.×1 in.×⅛ in. The prepared devices were then retained within a permeable cover and soaked in one of three repellent compositions comprising: 1. citronella oil and geraniol, 2. pure citronella oil, or 3. thyme oil. The saturated devices were subsequently wrapped in commercially available foil wrap and stored for approximately 2 weeks prior to use. The permeable cover on the devices of this test provided a first-order release or dispersal rate of the compositions in the devices.

Figure 8:
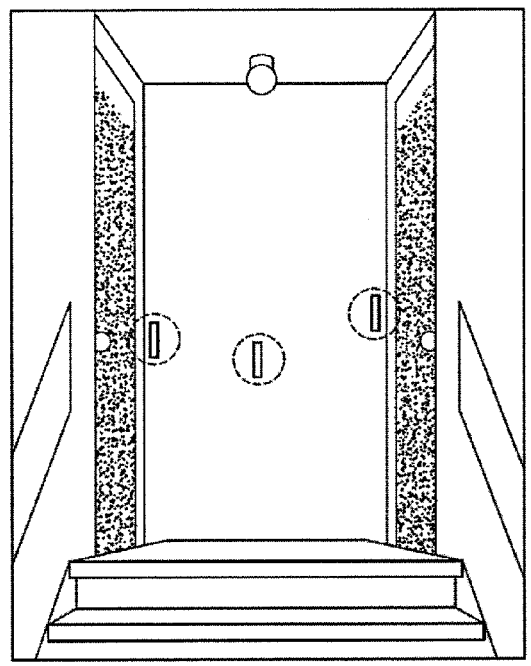
FIG. 8 is a photograph showing an example of a stairwell utilized for testing embodiments of the subject invention (see Example 2).

Three stairwells, such as the one shown in FIG. 8, were selected for use. Prior to testing, a count was obtained of the number of mosquitoes present in each stairwell. At the onset of the testing period, three devices of each composition were hung within each stairwell. Thus, one stairwell was treated with three devices soaked in citronella oil and geraniol, a second stairwell was treated with three devices soaked in pure citronella oil, and a third stairwell was treated with three devices soaked in thyme oil. In each stairwell, the devices were separately hung in different positions, each approximately halfway between the floor and the ceiling of the stairwell, as indicated by the circled areas in FIG. 8. The devices were maintained relatively undisturbed for about 2 days. At the end of the two day period, another count was obtained of the number of mosquitoes remaining in each stairwell.

Figure 9:
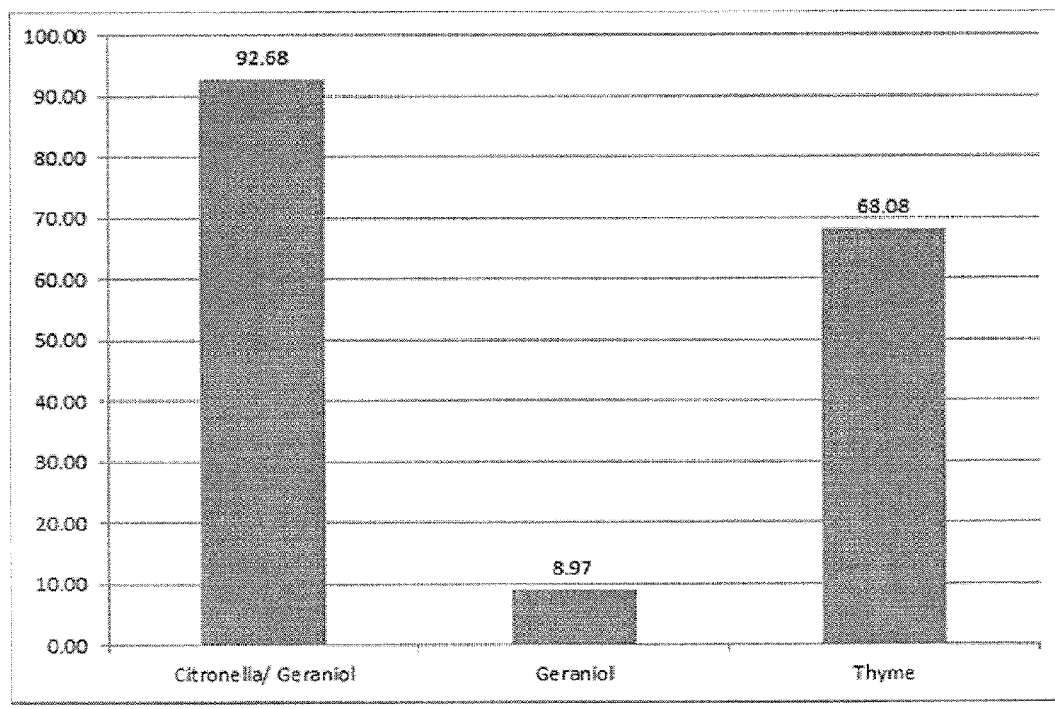
FIG. 9 is a graph showing the results of tests utilizing embodiments of the subject invention in different stairwells, where the embodiments contained different target compounds. (see Example 2)

FIG. 9 shows that the devices containing a citronella and geraniol composition were the most effective in repelling mosquitoes from the stairwells, with 92.68% reduction in the number of mosquitoes present. The devices containing thyme oil were the next most effective with a 68.08% reduction in the number of mosquitoes present and devices containing geraniol alone being the least effective.

Interestingly, studies previously conducted with caged mosquito populations demonstrated similar results, with regard to the order of effective repellency of the compositions.

The embodiments of the subject invention are particularly efficacious for long term, controlled release of insect repellent compounds. Effective devices can be manufactured from one or more GRAS materials or one or more materials that are included on the EPA FIFRA 25(b) list of permitted inert ingredients and minimum risk pesticides. The controlled release provided by the release devices makes it feasible to utilize natural, less toxic insect repelling substances, such as citronella oil, because they do not have to be diluted for use. Thus the inherent insect repelling properties of such compounds are brought fully to bear, which also allows smaller quantities to be employed in the devices. This makes them suitable for use in a variety of situations, such as in areas around human or animal insect targets and particularly as individualized insect release devices.

The scope of the invention is not limited by the specific examples and suggested procedures and uses related herein since modifications can be made within such scope from the information provided by this specification to those skilled in the art.

Any reference in this specification to "one embodiment," "an embodiment," "example embodiment," "further embodiment," "alternative embodiment," etc., is for literary convenience. The implication is that any particular feature, structure, or characteristic described in connection with such an embodiment is included in at least one embodiment of the invention. The appearance of such phrases in various places in the specification does not necessarily refer to the same embodiment. Further, when a particular feature, structure, or characteristic is described in connection with any embodiment, it is within the purview of one skilled in the art to affect such feature, structure, or characteristic in connection with other ones of the embodiments.

The invention has been described herein in considerable detail, in order to comply with the Patent Statutes and to provide those skilled in the art with information needed to apply the novel principles, and to construct and use such specialized components as are required. However, the invention can be carried out by specifically different equipment and devices, and various modifications, both as to equipment details and operating procedures can be effected without departing from the scope of the invention itself. Further, although the present invention has been described with reference to specific details of certain embodiments thereof and by examples disclosed herein, it is not intended that such details should be regarded as limitations upon the scope of the invention except as and to the extent that they are included in the accompanying claims.

We claim:

1. A release device comprising:
    an external housing formed from a material that absorbs and volatilizes one or more target compounds;
    at least one internal chamber located within the external housing, where the internal chamber has a mouth and is impermeable to the target compound;
    at least one reservoir disposed within the internal chamber, wherein the reservoir comprises a material that can be compromised to release into the internal chamber a liquid target compound stored within the reservoir; and
    a wick having a receiving end and a delivering end, where the receiving end is disposed within the internal chamber to absorb the target compound released from the reservoir and the delivering end passes through the mouth so as to be outside the internal chamber, where the internal chamber and wick are contained inside the external housing with the delivering end of the wick in contact with the external housing;
    such that the liquid target compound released when the reservoir is compromised is absorbed by the receiving end of the wick and transferred to the delivering end outside of the internal chamber where it is absorbed by all or most of the external housing and volatilized.

2. A release device, according to claim 1, further comprising a permeable cover at least partially surrounding the external housing, where the permeable cover controls the rate at which volatilized target compound is released from the external housing.

3. A release device according to claim 1, wherein the target compound released from the at least one reservoir compromises at least one other reservoir, so that target compound within that other reservoir is subsequently released.

4. A release device according to claim 2, wherein the external housing is pre-charged with target compound.

5. A release device according to claim 2, wherein the permeable cover comprises a material that allows volatilization therethrough.

6. A release device according to claim 2, wherein the permeable cover comprises a material with multiple perforations that allow volatilization therethrough.

7. A release device according to claim 1, wherein the at least one reservoir is mechanically compromised.

8. A release device according to claim 7, wherein the at least one other reservoir is chemically compromised.

9. A release device according to claim 1, wherein the external housing comprises one internal chamber with multiple reservoirs therein.

10. A release device according to claim 1, wherein the external housing comprises more than one internal chamber, each containing one or more reservoirs.

11. A release device according to claim 9, wherein the target compound, in at least one reservoir, is a triggering compound.

12. A release device according to claim 7, further comprising a container into which the external housing is disposed.

13. A release device according to claim 12, wherein the container mechanically compromises the at least one reservoir.

14. A release device, according to claim 1, wherein the external housing exhibits at or near a zero order volatilization.

15. A release device according to claim 1, wherein the external housing and the wick comprise substantially the same material.

16. A release device according to claim 1, wherein the external housing and the wick comprise different materials.

17. A method for controlling insects in a spatial area utilizing a release device comprising:
- an external housing formed from a material that absorbs and volatilizes one or more target compounds;
- at least one internal chamber located within the external housing where the internal chamber has a mouth and is impermeable to the target compound;
- at least one reservoir disposed within the internal chamber, wherein the reservoir comprises a material that can be compromised to release into the internal chamber a liquid target compound stored within the reservoir;
- a wick having a receiving end and a delivering end, where the receiving end is disposed within the internal chamber to absorb the target compound released from the at least one reservoir and the delivering end passes through the mouth so as to be outside the internal chamber, where the internal chamber and wick are contained inside the external housing with the delivering end of the wick in contact with the external housing;
- such that liquid target compound released when the reservoir is comprised is contained within the internal chamber, absorbed by the receiving end of the wick, and transferred to the delivering end outside of the internal chamber where it is absorbed by all or most of the external housing for volatilization;

wherein the method comprises,
compromising at least one of the at least one reservoir; and
placing the release device in a spatial area in which an insect is to be controlled.

18. A method according to claim 17, further comprising a container into which the release device is disposed.

19. A method according to claim 18, wherein the method further comprises utilizing the container to mechanically compromise the at

UNITED STATES PATENT AND TRADEMARK OFFICE
CERTIFICATE OF CORRECTION

| | | |
|---|---|---|
| PATENT NO. | : 9,258,988 B2 | Page 1 of 1 |
| APPLICATION NO. | : 14/332747 | |
| DATED | : February 16, 2016 | |
| INVENTOR(S) | : Bradley J. Willenberg et al. | |

It is certified that error appears in the above-identified patent and that said Letters Patent is hereby corrected as shown below:

In the Claims

Column 24,
Line 7, "material that can be" should read --material that is--.

Column 25,
Line 16, "material that can be" should read --material that is--.

Column 26,
Line 7, "is comprised" should read --is compromised--.

Signed and Sealed this
Third Day of May, 2016

Michelle K. Lee
*Director of the United States Patent and Trademark Office*